United States Patent [19]
Floratos et al.

[11] Patent Number: 6,108,666
[45] Date of Patent: Aug. 22, 2000

[54] METHOD AND APPARATUS FOR PATTERN DISCOVERY IN 1-DIMENSIONAL EVENT STREAMS

[75] Inventors: Aristidis Floratos; Isidore Rigoutsos, both of Long Island City, N.Y.

[73] Assignee: International Business Machines Corporation, Armonk, N.Y.

[21] Appl. No.: 09/023,756

[22] Filed: Feb. 13, 1998

Related U.S. Application Data

[60] Provisional application No. 60/049,461, Jun. 12, 1997.

[51] Int. Cl.⁷ .................................................. G06F 17/00
[52] U.S. Cl. .................................. 707/104; 707/3; 707/5; 706/12; 706/13
[58] Field of Search ...................... 707/1–206; 706/12–20

[56] References Cited

U.S. PATENT DOCUMENTS

| | | | |
|---|---|---|---|
| 5,343,554 | 8/1994 | Koza et al. | 706/13 |
| 5,390,282 | 2/1995 | Koza et al. | 706/13 |
| 5,577,249 | 11/1996 | Califano | 707/100 |
| 5,752,019 | 5/1998 | Rigoutsos | 707/104 |
| 5,787,279 | 7/1998 | Rigoutsos | 707/6 |
| 5,845,049 | 12/1998 | Wu | 706/16 |
| 5,907,834 | 5/1999 | Kephart et al. | 706/14 |

OTHER PUBLICATIONS

Wang, et al., "Combinatorial Pattern Discovery For Scientific Data:Some Preliminary Results", Sigmond 94–5/94, pp. 115–124.

Maier, "The Complexity of Some Problems on Subsequences and Supersequences", Journal of the ACM, 1978, p. 322–336.

Wang et al., "Discovering Active Motifs in Sets of Related Protein Sequences and Using Them for Classifications", Nucleic Acids Research, 1994, pp. 2769–2775.

Wang et al., "Complementary Classification Approaches for Protein Sequences", Protein Engineering, vol. 9, No. 5 pp. 381–386, 1996.

Neuwald et al., "Detecting Patterns in Protein Sequences", Journal of Molecular Biology, 1994, pp. 698–712.

Collins et al., "Finding Flexible Patterns in Unaligned Protein Sequences", Protein Science, 1995, pp. 1587–1595.

Wu, et al., "Identicfication of Protein Motifs Using Conserved Amino Acid Properties and Partitioning Techniques", Proceedings of the 3rd Int'l. Conf. on Intellingent Systems for Molecular Biology, 1995, pp. 402–410.

Martinez, A Flexible Multiple Sequence Alignment Program: Nucleic Acids Research, 1988, pp. 1683–1691.

Sobel, et al., "A Multiple Sequence Alignment Program", Nucleic Acids Research, 1986, pp. 363–374.

Hui, "Color Set Size Problem with Applications to String Matching", Proceedings of the 2nd Symposium on Combinatorial Pattern Matching, 1992, pp. 230–243.

(List continued on next page.)

*Primary Examiner*—Thomas G. Black
*Assistant Examiner*—David Yink Jung
*Attorney, Agent, or Firm*—Jay P. Sbrollini

[57] ABSTRACT

The method of the present invention discovers patterns in a sequence of characters in two phases. In a sampling phase, preferably proper templates corresponding to the sequence of characters are generated. Patterns are then generated corresponding to the templates and stored in memory. In a convolution phase, the patterns stored in memory are combined to identify a set of maximal patterns.

42 Claims, 9 Drawing Sheets

OTHER PUBLICATIONS

Smith, et al., "Finding Sequence Motifs in Groups of Functionally Related Proteins", Proceedings of the National Academy of Sciences, pp. 826–830, 1990.

Roytberg, "A Search for Common Patterns in Many Sequences", Cabios, pp. 57–64, 1992.

Smith, et al., "Automatic Generation of Primary Sequence Patterns from Sets of Related Protein Sequences", Nucleic Acids Research, 1990, pp. 118–122.

Guan, et al., "A Fast Look–Up Alogorithm for Detecting Repetitive DNA Sequences", Pacific Symposium on Biocomputing, 1996, pp. 718–719.

Nevill–Manning, et al., "Enumerating and Ranking Discrete Motifs", Intelligent Systems for Molecular Biology, 1997, pp. 1–8.

Benson, et al. "A Method for Fast Database Search for All K–Nucleotide Repeats", Proceedings of the 2nd International Conference on Intelligent Systems for Molecular Biology, 1994, pp. 83–98.

Sagot, et al., "A Double Combinatorial Approach to Discovering Patterns in Biological Sequences" Proceedings of the 7th Symposium on Combinatorial Pattern Matching, 1996, pp. 186–208.

Brazma, et al., "Approaches to the Automatic Discovery of Patterns in Biosequences", Technical Report, Department of informatics, Unversity of Bergen, 1995.

Smith–Waterman, "Identification of Common Molecular Subsequences", J. Mol. Biol. (1981) 147, 195–197.

Bairoch, et al., "The Prosite Database, Its Status In 1995", Nucleic Acids Research, 1996, vol. 24, No. 1, pp. 189–196.

Califano, et al., "Flash: Fast Look–Up Algorithm for String Homology", Cabios, Feb. 9, 1995, pp. 1–22.

Califano, et al., "Flash: A Fast Look–Up Algorithm for String Homology", Proceedings 1st Int'l. Conference on Intelligent Systems for Molecular Biology, Jul. 6–9, 1993, pp. 56–64.

METHOD AND APPARATUS FOR PATTERN DISCOVERY IN 1-DIMENSIONAL EVENT STREAMS

CROSS-REFERENCE TO RELATED APPLICATIONS

The present application claims priority to Provisional U.S. Patent Application No. 60/049,461, filed Jun. 12, 1997, by A. Floratos and I. Rigoutsos, herein incorporated by reference in its entirety, and is related to i) U.S. patent application No. Ser. 09/023,792, filed concurrently herewith, by A. Floratos and I. Rigoutsos, ii) U.S. patent application Ser. No. 09/023,759, filed concurrently herewith, by by A. Floratos and I. Rigoutsos, and iii) U.S. patent application Ser. No. 09/023,758, filed concurrently herewith, by by A. Floratos and I. Rigoutsos.

BACKGROUND OF THE INVENTION

1. Technical Field

The invention relates to the field of pattern discovery, and, more specifically, to pattern discovery in 1-dimensional event streams.

2. Description of the Related Art

An event stream is a sequence of events which are taken from a finite set of possible events. This latter set can be thought of as an alphabet in which case an event stream is a string over that alphabet. The term sequence used below may refer to an event stream or a sequence of characters belonging to an alphabet. A pattern is a specific set of letters with a given spatial arrangement, typically described as a regular expression.

An example of such a pattern is "AF..H..RR" where the dots are used to indicate that the respective positions could be occupied by "any" letter ("don't care" character). An event string is said to match the pattern at a given position i, if and only if the letters of the pattern all match the corresponding letters of the event string, when placed at offset i; a don't care character is assumed to match any letter of the alphabet. For example, "AF..H..RR" matches "HWIR-TAFLKHAARRIKWL" at position 6.

The problem of pattern discovery is computationally a very demanding one. Indeed, it can be proven to be NP-hard (unless the type of patterns sought is extremely simple). The problem can be stated as follows:

"Given a set $S=\{s_1, s_2, \ldots, s_m\}$ of one ore more sequences $s_i$ (i.e. strings) over an alphabet $\Sigma$ of letters and positive integer K, find all the patterns which match K or more of the input sequences in S."

In this first formulation, what is sought is those patterns that appear in at least K of the sequences of the input set. However, it may happen that a pattern appears in fewer than K of the sequences, but more than once in some of those sequences. In other words, one or more sequences may contain multiple occurrences of a given pattern. Consequently, such a pattern may appear in fewer than K sequences but more than K times when all sequences of S are considered. The definition of the problem can then be modified to capture this case as well:

"Given a set $S=\{s_1, s_2, \ldots, s_m\}$ of one or more sequences $s_i$ over an alphabet $\Sigma$ of letters and positive integer K, find all the patterns which appear K or more times in the sequences in S."

The invention that is described below can handle both of these versions of the pattern discovery problem.

The problem of discovering patterns in event streams appears very often and in many different application areas (biology, data mining in databases, computer security etc.). Depending on the particular domain at hand there are many different definitions of the notion of the pattern as well as of what it means for an input to match a particular pattern.

Almost invariably the input is a set S composed of arbitrary strings over a given alphabet $\Sigma$ and a pattern is any member of a well defined subset C of all the possible regular expression over $\Sigma$ (e.g. C can be the set of all regular expression with some predefined maximum length). The reasons why the search for patterns is restricted to some subset of all possible regular expressions are both domain-specific and also of a practical nature since (as is explained later) the problem is computationally extremely demanding.

Being a regular expression, every pattern P defines a language L,(P) in the natural way: a string belongs to L(P) if it is recognized by the automation of P. An input string w is said to match a given pattern P if w contains some substring that belongs to L(P). The problem then is to discover all patterns in C matched by at least a given (user-defined) minimum number of strings in the input set S.

For an illustration, consider the following set of strings over the English alphabet:

$$S=\{\text{"LARGE"}, \text{"LINGER"}, \text{"AGE"}\}$$

In this case the pattern "L..GE" has support 2 since it is matched by the first two strings of S (the special character '.' in the pattern indicates a position that can be occupied by any character). The term support is used here to denote the number of input strings matching a given pattern. As another example, the pattern "A*GE" has also support 2 (it is matched by the first and the last strings). Here, the character '*' is used to match substrings of arbitrary length, which can include strings of zero length.

The computational complexity of the pattern discovery problem directly depends on the class C of regular expressions that the patterns belong to. In the most straightforward case a pattern is simply a string over the alphabet $\Sigma$ (i.e. just a sequence of alphabet symbols—no don't care characters) and the problem of finding all such patterns with a given minimum support can be solved in polynomial time using generalized suffix trees. An example of such a pattern discovery problem is illustrated in Hui, *"Color Set Size Problem with Applications to String Matching"*, Proceedings of the 2nd Sumposium on Combinatorial Pattern Matching, 1992, pp. 230–243.

In almost every other case though, the class C is expressive enough to render the problem NP-hard. The hardness result can be usually shown by a reduction from the longest common subsequence problem, discussed in Garey and Johnson, *"Computers and Intractability: a Guide to the Theory of NP-Completeness"*, 1979, and Maier, *"The Complexity of Some Problems on Subsequences and Supersequences"*, Journal of the ACM, 1978, pp. 322–336. What this means in practice is that there can be no algorithm guaranteed to produce, for every possible input, all the required patterns in time polynomial to the input length.

One way to bypass the hardness of the problem is to design approximation algorithms, i.e. algorithms that are guaranteed to work "fast" for every input but do not necessarily find all the existing patterns for every given input. Another approach is to further restrict the patterns that the algorithm can discover so that they can be found efficiently. This is usually left to the discretion of the user by providing him/her with the ability to appropriately set a number of parameters that decide the structure of the patterns to be looked for. A typical example is to allow the user to define the maximum length that a pattern can have. Providing the user with that kind of control over the search space is not unreasonable since an expert user can apply domain knowledge to help a program avoid looking for patterns that are meaningless or impossible for the domain at hand. In fact, this expert knowledge is usually an integral part (in the form of various heuristics) of most of the pattern discovery algorithms that exist in the literature (the disadvantage of this approach is that most of these algorithms are usually inapplicable outside the particular domain which they were designed for). Finally, there are the algorithms that just accept the hardness of the problem and proceed head-on to find all possible patterns. Such algorithms are bound to be inefficient (space and/or time-wise) on some "bad" inputs but, depending on the domain at hand, their overall performance (amortized over all "reasonable" inputs) might be quite satisfactory. In such cases, it becomes very important to introduce a number of heuristics that will speed up the algorithm. The method presented here belongs to this category.

The standard way to assess the "quality" of an algorithm (at least in the context of computer science) is by its time/space complexity. For the pattern discovery problem, though, such a characterization is rather useless. The reason is the NP-hardness of the problem: any worst-case analysis is doomed to give bounds which are super-polynomial (unless the complexity classes P, NP are equal, something extremely unlike). There are, however, other features that are of interest when evaluating a pattern discovery algorithm. Some of these features are:

- The subclass C of regular expressions containing the patterns under consideration. In general, it is desirable to have as expressive a class C as possible. The price for the increased expressiveness is usually paid in terms of time/space efficiency.
- The ability of the algorithm to generate all qualified patterns. As mentioned earlier, some approximation algorithms can achieve increased performance by sacrificing the completeness of the reported results. Depending on the domain of the application and the quality of the patterns discovered, this might or might not be an acceptable tradeoff.
- The maximality of the discovered patterns. Consider for example the instance of the input set S given at the beginning of this section. In this case "L...E" is a perfectly legal pattern. It is not however maximal, in the sense that the pattern "L..GE", while more specific, still has the same support as "L...E". Reporting patterns which are not maximal not only unnecessarily clutters the output (making it difficult to separate the patterns which are really important) but can also severely affect the performance of the algorithm. It is then extremely important for a pattern discovery algorithm to be able to detect and discard non-maximal patterns as early as possible.

The pattern discovery algorithms can, in general, be categorized in either of the following two classes: string alignment algorithms and pattern enumeration algorithms. Below we present a short survey of both categories. A more detailed description of the two classes of pattern discovery algorithms can be found in Brazma et al., "*Approaches to the Automatic Discovery of Patterns in Biosequences*", Technical Report, Department of Informatics, University of Bergen, 1995. The list of algorithms discussed is certainly not exhaustive but it highlights the main trends in the respective classes.

Algorithms in the string alignment class use multiple alignment of the input strings as the basic tool for discovering the patterns in question. Given a set $S=\{s_1, \ldots, s_n\}$ of strings over an alphabet $\Sigma$ and a number of edit operations (e.g. mutation of a character into another character, deletion of a character, insertion of a character etc.), a multiple alignment of the strings in S is defined as:

a string $w \in \Sigma^*$, called a consensus sequence for each $1 \leq i \leq n$, a sequence of edit operations for transforming $s_i$ into w.

As soon as a multiple string alignment is acquired, the task of locating the patterns reduces to searching the consensus sequence for substrings with high enough support.

The problem of course is not that simple: the consensus sequence must be appropriately chosen so as to reveal the patterns shared by the input strings. This entails the assignment of costs to the various edit operations and the selection of an optimal consensus sequence that minimizes the cost of transforming the input strings into that particular sequence. A complete description of the problem is outside the scope of this document. What is important to note, though, is the fact that the problem of finding such an optimal sequence is NP-hard. As a result, most algorithms in this class resort to heuristics that produce sub-optimal alignments, thus trading-off enhanced execution speed with results that are generally not complete. There are also other problems related to multiple string alignment (e.g. the problem of domain swapping) which further complicate the generation of a complete list of patterns for a given input set. In general, using multiple string alignment for the discovery of patterns can be effective only when the aligned strings share global similarities as discussed in Smith et al., "*Finding Sequence Motifs in Groups of Functionally Related Proteins*", Proceedings of the National Academy of Sciences, pp. 826–830, 1990; Hirosawa et. al. "*Comprehensive Study On Iterative Algorithms Of Multiple Sequence Alignment*", CABIOS, 1995; and Suyama et al., "*Searching for Common Sequence Patterns Among Distantly Related Proteins*", Protein Engineering, pp. 1075–1080, 1995.

Almost all the algorithms in this class have been developed for finding patterns shared by a number of (allegedly related) biological sequences. The reason is that the edit operations of mutation, insertion and deletion are the mechanisms used by evolution to differentiate among species. This makes the utilization of multiple string alignment a natural tool for attacking the pattern discovery problem in the context of Biology.

Most of the string alignment algorithms use pairwise alignments and then apply a number of heuristics in order to approximate an optimal multiple alignment of the input strings. In Martinez, M., "*A Flexible Multiple Sequence Alignment Program*" Nucleic Acids Research, 1988, pp. 1683–1691, all possible pairs of input strings are aligned and scored. Then an ordering of the input strings is generated, based on the alignment scores (the intention is for strings that are similar to be placed close together in that ordering). The final multiple alignment is built in a piece-wise manner, by traversing the ordered list of the input strings: each time a new string is added the old alignment is modified (by adding insertions where appropriate) so that the character to character matches of the original, pairwise alignments are preserved.

A slightly different approach is pursued in Smith and Smith, "*Automatic Generation of Primary Sequence Patterns from Sets of Related Protein Sequences*", Nucleic Acids Research, 1990, pp. 118–122. Again the starting point is generating and scoring all possible pairwise alignments. Scoring is performed based on a partition of the amino acid alphabet into amino acid class covering (AACC) groups, based on the physicochemical properties of the amino acids. Using the scores obtained at the first step a binary tree, called dendrogram, is built having the input sequences as its leaves; the intention is to cluster together those of the input sequences which are similar. Then the internal nodes of the dendrogram are traversed bottom-up and each node is assigned a label. This label is a pattern, obtained by aligning the two children of the node (a child is either an original sequence—if it is a leaf—or a pattern obtained through a previous alignment); in the course of the alignment procedure, aligned characters that differ are represented by the smallest AACC group that contains both of them. At the end, each internal node has been labelled by a pattern which is contained in all the input sequences that are leaves of the subtree rooted at that internal node.

Another algorithm (Emotif) employing multiple string alignment as the main tool for the discovery of patterns is presented in Neville-Manning et al., *"Enumerating and Ranking Discrete Motifs"*, Intelligent Systems for Molecular Biology, 1997, which extends the work of Wu and Brutlag in *"Identification of Protein Motifs Using Conserved Amino Acid Properties and Partitioning Techniques"*, Proceedings of the 3rd International Conference on Intelligent Systems for Molecular Biology, 1995, pp. 402–410. Here, along with the set S of the input strings the user also provides a collection $R \subseteq 2^\Sigma$ of subsets of the alphabet $\Sigma$. A pattern can have at a given position any element $E \in R$ and a character c of an input string matches that pattern position if $c \in E$. The set R provides a generalization of the AACC groups used in Smith and Smith, *"Automatic Generation of Primary Sequence Patterns from Sets of Related Protein Sequences"*, Nucleic Acids Research, 1990, pp. 118–122. Emotif starts by generating a multiple alignment of the input strings. The alignment is used to guide the generation of the patterns in a recursive way: at each point a subset S' of the original set S is being considered (originally S'=S) and a particular column in the alignment of the strings in S' (originally the first column). Also, there is a pattern P currently under expansion (originally P is the empty string). The pattern P is expanded to P'=PE where $E \in R$ contains at least one of the characters found in the strings of S' at the alignment column under consideration. The expansion proceeds as long as the new pattern has sufficiently large support and is not redundant, i.e. does not appear at the same sequences (and positions within the sequences) where a previously generated pattern has appeared. At the next expansion step the set S' will be set to those strings that match the new pattern P' and the next column of the alignment will be considered.

A different heuristic is proposed by Roytberg in *"A Search for Common Patterns in Many Sequences"*, CABIOS, pp. 57–64, 1992. Although his method does not directly use alignment, it works in a way reminiscent of the other algorithms in this class (in that it gets information about potential patterns by pairwise comparisons of the input strings). Here, one of the input sequences is selected as the basic sequence and is compared with all other sequences for similar segments (the notion of similarity is a parameter of the algorithm). A segment of the basic sequence gives rise to pattern if at least k sequences (the minimum required support) have segments similar to it. The major drawback of this method is that it is crucially dependent on the selection of the basic sequence. This drawback can be partially offset by employing repeated runs of the algorithm, each one with a different basic sequence.

A comprehensive comparative study of a number of multiple string alignment algorithms can be found in Hirosawa et al., *"Comprehensive Study on Iterative Algorithms of Multiple Sequence Alignment"*, CABIOS, 1995.

Algorithms in the pattern enumeration class enumerate all (or some) possible patterns and then verify which of these patterns have the required support. Since such algorithms explore the space of patterns they tend to be exponential on the maximal pattern size. In order to be efficient, they usually impose some kind of restriction to the structure of the patterns to be discovered.

Very roughly, the underlying idea used by all these algorithms is the following: start with the empty pattern and proceed recursively to generate longer and longer patterns. At each step enumerate all (or some) allowable patterns (i.e. those patterns that belong to the subclass C of regular expressions treated by the algorithm) that have the current pattern as prefix. For every new pattern check its support. If it is big enough continue the expansion. If not just report the current pattern and backtrack to the previous step of the expansion procedure.

The various algorithms differ in the class C of patterns that they recognize, the efficiency which they implement pattern expansion, and their ability to detect and discard redudant patterns.

One of the first algorithms in this class, which is presented in Sobel and Martinez, *"A Multiple Sequence Alignment Program"*, Nucleic Acids Research, 1986, pp. 363–374, was actually a part of a method used for the multiple string alignment problem (some alignment programs approximate optimal alignments by first locating patterns common to all strings and then using this patterns as the anchor points for the alignment). The algorithm works by first locating substrings X common to all the input sequences, each substring having length at least L. For every such X the set of all possible regions is defined, each region being an n-tuple $(p_1, \ldots, p_n)$ (n is the number of input sequences) where $p_i$ is an offset within the i-th sequence where X appears. These regions become vertices in a directed graph. If $R_X=(x_1, \ldots, x_n)$, $R_Y=(y_1, \ldots, y_n)$ are regions corresponding to the substrings X and Y, then a line from $R_X$ to $R_Y$ is added in the graph if the two regions are non-overlapping and $R_X$ comes before $R_Y$. In other words, if for every i $$x_i + X - 1 < y_i.$$

Finally the graph is traversed for a longest possible path (they give a particular function for assigning costs to the edges but any meaningful cost function could be used in its place).

There is a number of weaknesses with this method. First, it can only find patterns supported by all the input sequences. Furthermore, in order for it to be efficient the parameter L for the minimum length of substrings to look for must be quite large. Otherwise a huge number of regions will be generated. As a result, patterns containing shorter substrings will go unnoticed.

A straightforward example of pattern enumeration appears in the work Smith et. al., *"Finding Sequence Motifs in Groups of Functionally Related Proteins"*, Proceedings of the National Academy of Sciences, 1990, pp. 826–830. Again, the domain is that of Biology. They proceed by enumerating all patterns containing 3 characters and having the form $$c_1 x(0, d_1) c_2 x(0, d_2) c_3$$

where $c_i$ are alphabet characters and x(i, j) indicates a flexible wildcard gap matched by any string with length between i and j (as a matter of terminology, we also speak of rigid gaps which have the form x(i) and are matched by any string of length exactly i). Each pattern thus generated is searched over all the input strings. If it has sufficient support all sequences where it appears are aligned along this pattern and the pattern is further expanded according to the alignment. The main disadvantage of this method is that it actually enumerates all possible patterns, making it hard to handle patterns with more than 3 characters and with large values for the parameters $d_1$ and $d_2$.

Suyama et. al. in *"Searching for Common Sequence Patterns Among Distantly Related Proteins"*, Protein Engineering, 1995, pp. 1075–1080, describe an algorithm very similar to the above. They start by enumerating all triplets $c_1 c_2 c_3$ and creating a cluster for every such triplet. Each cluster contains all the input sequences that contain the characters $c_1$, $c_2$, $c_3$ (in that order) within a window of length W (a user defined parameter). Subsequently the clusters are further refined by adding a fourth character at the end of every triplet and breaking them up so that only sequences that contain all four characters (always in order) are in each cluster. Finally, a last refinement is performed with the addition of a fifth character. At that point each cluster undergoes a final break down by now requiring that the sequences not only contain the same five characters but that the number of positions between successive characters are also the same. One of the defects of this algorithm is that it handles only patterns with up to five characters. Of course, the same procedure can be extended to handle more than five characters but the efficiency drops very quickly as the number of characters and the size of the input set increases.

Neuwald and Green, *"Detecting Patterns in Protein Sequences"*, Journal of Molecular Biology, 1994, pp. 698–712, also use as a starting point the algorithm of Smith et. al., *"Finding Sequence Motifs in Groups of Functionally Related Proteins"*, Proceedings of the National Academy of Sciences, 1990, pp. 826–830. Their method allows the discovery of rigid patterns of arbitrary length (obeying some structural restrictions set up by user defined parameters). Furthermore, they allow double character pattern positions of the form $[c_1 c_2]$ which can be matched by either of the characters $c_1$, $c_2$ (the number of these positions, though, must be kept to a minimum or the performance of the algorithm suffers). Their algorithm starts by enumerating all possible patterns with a given maximum length, given number of non-don't care positions and a maximum allowed number of double character positions. The enumeration is carried out efficiently in a depth-first manner using blocks, a special data structure recording, for every character, all offsets of the input strings that the character has a fixed distance from. The enumeration is further sped up by pruning the patterns that do not achieve sufficient support. Using statistical analysis, they keep just a portion of the patterns thus generated (those that are deemed "important"). At the final step, these patterns are combined into longer patterns by pairwise comparison: two patterns are expanded into a new one if they have adequate "compatible" appearances, i.e. if there are enough sequences where the two patterns appear separated by a fixed displacement. This expansion operation is made possible because of the block structure representation of the patterns which contains the list of offsets the patterns appear in.

Based on the work of Neuwald and Green above, Collins et. al., *"Finding Flexible Patterns in Unaligned Protein Sequences"*, Protein Science, 1995, pp. 1587–1595, gives an even more powerful pattern discovery algorithm. Theirs allows flexible patterns of the following form:

$$P = A_1\, x(i_1, j_1) A_2\, x(i_2, j_2) \ldots A_{(p-1)} x(i_{(p-1)}, j_{(p-1)}) A_p$$

where $$i_k \leq j_k.$$

The $A_i$'s are character sets (consisting of one or more characters) and are called components. A component can be either of the identity or ambiguous type, depending on whether it contains one or more than one character. The wild-card regions $x(i, j)$ are either rigid (if $i=j$; such a region is written in the simpler form $x(i)$) or flexible if ($j>i$). The input to the algorithm (except from the actual sequences) contains a host of other parameters that restrict the kind of patterns to look for (e.g. maximum pattern length, maximum number of components, maximum number of ambiguous components, the kind of ambiguous components allowed etc.) as well as the minimum support k for a pattern. The algorithm proceeds in two phases. In the first one, the block structure described in Neuwald and Green, *"Detecting Patterns in Protein Sequences"*, Journal of Molecular Biology, 1994, pp. 698–712, is used to enumerate all patterns with length up to the maximum possible. As a preprocessing step, blocks $b_{i, R}$ are created for every allowable component R (be it either a single character or a set of characters). Every such block contains offsets in the input sequences. A particular offset is in $b_{i, R}$ if some character in R is at distance i from that offset. If only rigid patterns have been requested and P is the current rigid pattern at any given time, then they check all possible patterns P' of the form $P'=P\, x(j)R$ where $x(j)$ is a rigid wild-card region of length j and R is either a single character or an allowable ambiguous component. If $B_P$ is the block structure for P (every structure carries along with it the list of offsets where it appears), then $$B_{P'} = B_P \cap b_{L(P)+j+1,\, R}$$

where L(P) is the length of the pattern P (i.e. the size of every string matching P).

If, on the other hand, flexible patterns have also been allowed then a flexible pattern P is represented as the set F(P)) of all the rigid patterns that make it up. For example, if $$P = D\, x(1, 2) E\, x(2, 3) F,$$

then the set F(P) is comprised by the fixed patterns
D x(1)E x(2)F,
D x(1)E x(3)F,
D x(2)E x(2)F,
D x(2)E x(3)F and every pattern Q∈F(P) carries its own block structure. In this case the current pattern P is extended into $P'=P\, x(i, j)R$ using all possible values of $i \leq j$. The block structure for P' is actually constructed by extending every pattern Q∈F(P) into a pattern $Q_k$, ($i \leq k \leq j$) using the relation $$B_{Q_k} = B_Q \cap b_{L(Q)+k+1, R}$$

and then the set F(P') becomes $$F(P') = \bigcup_{\substack{Q \in F(P) \\ i \leq k \leq j}} Q_k$$

In both cases (flexible regions allowed or not) further expansion of P' is pruned if the block size of P' is less than the minimum support k (if P' is a flexible pattern then its block size is just the sum of the block sizes of all fixed patterns in F(P')).

In the second phase, the patterns discovered are further processed in a number of ways. Possibilities include replacing some don't care characters by an extended alphabet of ambiguous components, extending a pattern, etc.

A similar algorithm is described by Sagot and Viari in *"A Double Combinatorial Approach to Discovering Patterns in Biological Sequences"*, Proceedings of the 7th Symposium on Combinatorial Pattern Matching, 1996, pp. 186–208. Their algorithm also allows ambiguous components but it only treats rigid gaps. Again, the user must define (among other parameters like the maximum pattern length) which ambiguous components to use as well as, for every ambiguous component, the maximum number of times it is allowed to appear in a given pattern. They also proceed by recursively enumerating all allowable patterns, in a way very similar to that described in Jonassen et al., D.G., *"Finding Flexible Patterns in Unaligned Protein Sequences"*, Protein Science, 1995, pp. 1587–1595. The entire process is made faster by the introduction of two heuristics.

First, an effort is made to avoid creating redundant patterns. Let P be the pattern currently expanded. If S, S' are both allowable ambiguous components with S⊂S' and PS, PS' are both possible extensions of P and the offset lists of PS and PS' are the same then only the pattern PS is maintained—the expansion is pruned at PS'. This heuristic does not detect all non-maximal patterns: because of the way their algorithm builds the patterns, some redundancies will go unnoticed.

Second, a clever trick is used in order to reduce the input size. Instead of considering the ambiguous components specified by the user, they originally replace all of them by the don't care character. This greatly simplifies the pattern space to search and makes the entire discovery process much faster. After this step only the part of the input that matches the (reduced) patterns found is maintained and it is on this subset of the input that the algorithm is rerun, now using the full pattern specification given by the user.

A different approach in enumerating and verifying potential patterns is proposed by Wang et. al. in *"Discovering Active Motifs in Sets of Related Protein Sequences and Using them for Classification"*, Nucleic Acids Research, 1994, pp. 2769–2775. The pattern language they treat is composed by m-component patterns of the form $$P = X_1 * X_2 * \ldots * X_m$$

where the number m is a user specified parameter.

The components $X_i$ are alphabet strings and the '*' stands for flexible gaps of arbitrary length. The length P of the pattern is defined as the sum, over all i of the lengths $X_i$.

The algorithm works in two phases. First, the components $X_i$ of a potential pattern are computed. This is done by building a generalized suffix tree (GST) for the suffixes of all input sequences. Each leaf corresponds to a suffix and is labeled with the sequence containing this suffix (notice that more than one leafs can be attached to a given suffix since the suffix might appear in many sequences). Every internal node u contains the number count(u) of distinct sequences labelling the leafs of the subtree rooted at that node. So, if locus(u) is the string labelling the path from the root of the GST to an internal node u, then count(u) is the number of distinct sequences containing the substring locus(u). The first phase ends by creating the set Q containing all strings locus(u) such that count(u)≧k, where k is the minimum support.

The second phase verifies which m-component patterns (among those that can be built from the elements of Q) have the minimum support. This is a computationally demanding process since every potential pattern has to be compared against all the input strings. To speed things up, the space of all potential m-component patterns is pruned using the following statistical heuristic: first a (small) random subset S' of the original set S of input sequences is chosen. For every potential pattern P its support in S' is computed by matching it to the strings in S'. Then, using sampling theory, the probability that the actual support of P in S is k or more is computed, given the support of P in S'. If this probability is very small, then the pattern P is thrown away. So, at the end of the heuristic, patterns which are unlike to have the required support in S have been discarded. The remaining patterns are then verified by computing their support over the original input set S. Those that appear in at least k of the input sequences are reported in the final results.

The use of the above mentioned statistical heuristic makes it possible to treat sets S with many sequences (although it entails the possibility of not detecting some important patterns that are not "lucky" enough to pass the statistical test). Furthermore, the approach is really effective only if the minimum support k is comparable to the number of sequences in S. Another drawback of the algorithm is that its performance deteriorates very fast as the parameter m, defining the structure of the patterns searched for, increases. Finally, there is no provision for the detection of redundant patterns.

Another example of a pattern discovery algorithm is given by Agrawal and Srikant in *"Mining Sequential Patterns"*, International Conference on Data Engineering, 1995. The domain here is that of data mining. The formulation of the problem in this setting is slightly different. More specifically, the input consists of strings defined over ($2^\Sigma - \emptyset$), where $\Sigma$ is the underlying alphabet. In other words, a string is a sequence of subsets of $\Sigma$ rather than a sequence of elements of $\Sigma$. Given now two such strings $A=(a_1\ a_2\ \ldots\ a_n)$ and $B=(b_1\ b_2\ \ldots\ b_m)$, $m \geq n$, we say that A is contained in B if there are indices $1 \leq i_1 < i_2 < \ldots < i_n \leq m$ such that $$a_1 \subseteq b_{i1} \wedge a_2 \subseteq b_{i2} \ldots \wedge a_n \subseteq b_{in}$$

Given a set S of strings and a query string q, then q has support at least k in S if it is contained in at least k sequences of S. Also, q is called maximal if there is no other sequence q' with support at least k such that q is contained in q'.

The problem solved by the pattern discovery algorithm of Agrawal et al. is to find, given a set S of strings and a number k, all maximal strings with support at least k in S. The algorithm proposed works in a number of phases. In the first phase all subsets of $\Sigma$ that have support at least k are found. Call this set E. Then, in order to simplify the subsequent operations, a distinct integer label is assigned to every element of E. In the second phase, called transformation, each $s=(I_1, \ldots, I_s) \in S$ is examined in turn and every $I_j \subseteq \Sigma$ is replaced by those elements of E (actually, their integer labels) which are subsets of $I_j$. The main work of the algorithm is done in the third phase, the sequencing phase.

In the sequencing phase, the strings that potentially have the minimal support are enumerated and verified. A number of different methods are proposed in order to carry out these tasks. The main idea in all of them is the following recursive procedure: let $L_i$ be the set of all strings with length i that have support at least k in S (initially $L_1=E$, where E is the set computed in the first phase of the algorithm). The set $L_i$ is used in order to generate the set $C_{i+1}$ of candidates, containing the length (i+1) strings that may have minimum support. The intuition behind the generation of $C_{i+1}$ is that if $w=w_1 \ldots w_{i+1}$ has support at least k, then the same must be true for every length i subsequence of w. The set $C_{i+1}$ is generated by joining the set $L_i$ with itself in the following way For every (ordered) pair (x, y) of elements of $L_i$ where $x=(x_1 \ldots x_i)$, $y=(y_1 \ldots y_i)$ which are such that $x_j=y_j$ for all $1 \leq j \leq (i-1)$, generate the candidate string $s'=(x_1 x_2 \ldots x_{i-1} x_i y_i)$ and add it into $C_{i+1}$.

Go through $C_{i+1}$ removing those sequence $s \in C_{i+1}$ which contain an i-subsequence not in $L_i$.

After $C_{i+1}$ has been generated, it is verified against the set S of the input strings: for every candidate string $x \in C_{i+1}$ the strings $s \in S$ containing x are located. If their number is at least k then x is added in $L_{i+1}$, otherwise x is discarded. The whole process continues until some i is found for which $L_{i+1}$ turns out to be empty.

The final phase of the algorithm makes sure that only maximal strings are reported. This is achieved by going through every $x \in L_i$ (in decreasing order of i), and deleting all $y \in L_j$ ($j \leq i$) such that y is contained in x.

Other algorithms for various versions of the pattern discovery problem have also been proposed. In Guan and Uberbacher, *"A Fast Look-Up Algorithm for Detecting Repetitive DNA Sequences"*, Pacific Symposioum on Biocomputing, 1996, pp. 718–719, an algorithm for the identification of tandem repeats in DNA sequences is described. A tandem repeat is a restricted form of a pattern containing consecutive repetitions of the same substring. E.g. "AATAATAATAATAATAAT" is a tandem repeat of the substring "AAT". The substring being repeated is called the seed of the tandem repeat. Guan and Uberbacher give a linear time algorithm for the identification of short tandem repeats (where the seed of the repeat is a few characters long) using a hashing scheme introduced in Califano, A. and Rigoutsos, I., *"FLASH: A Fast Look-Up Algorithm for String Homology"*, CABIOS. Their method computes for every offset in the input at hand a number of hash values (using a few characters within a small window around the offset under consideration). The seeds of a tandem repeat are identified by locating offsets that have several such hash values in common. Benson and Waterman, *"A Method for Fast Database Search for all k-nucleotide Repeats"*, Proceedings of the 2nd International Conference on Intelligent Systems for Molecular Biology, 1994, pp. 83–98, provides another approach for the same problem. They begin by identifying suspicious patterns (i.e. substrings that can, potentially, be seeds for a tandem repeat) and check the area around the suspicious pattern to see if that pattern appears (either unchanged or mutated) in several consecutive copies. Their method incorporates elements from alignment algorithms in checking for the copies of the suspicious pattern.

Each of the two classes of algorithms described above have their pros and cons. By allowing the operations of insertion and deletion, string alignment methods can locate flexible patterns, a category of increased expressiveness (and, thus, complexity). Also, by using fast approximations to optimal multiple string alignments, patterns can be quickly discovered. On the other hand, no matter how one chooses to assign cost for the allowable edit operations, there will always be inputs containing patterns that cannot be encapsulated by the optimal consensus sequence (and this remains true even if near-optimal consensus sequences are considered). This problem becomes more acute for inputs where the sequences do not have global similarities. As a result, string alignment methods can be a viable approach only if the completeness of the reported resulted is not an absolute necessity, the input sequences can be clustered into groups that have global similarities, so that the alignment can produce "relevant" consensus sequences.

The pattern enumeration algorithms, on the other hand, have the potential of generating all non-redundant patterns. The price to be paid for completeness, though, can be steep since a huge space of potential patterns has to be searched. This search problem is magnified many-fold if one is to allow flexible patterns and/or patterns that allow multiple character positions. Furthermore, making sure that only maximal patterns are reported is a task which is far from trivial (if efficiency is to be achieved).

SUMMARY OF THE INVENTION

The problems stated above and the related problems of the prior art are solved with the principles of the present invention, method and apparatus for pattern discovery in 1-Dimensional Event Streams. In a sampling phase, patterns are generated and stored in memory. These patterns may be generated using templates corresponding to a sequence of characters. Preferably, such templates are proper templates. Patterns are then generated corresponding to the templates and stored in memory. Alternatively, the patterns of the sampling phase can be generated by starting with a seed pattern and extending it by a single position at a time, checking at every step of the process if the new pattern has the required support and pruning the search if it does not. In a convolution phase, the patterns stored in memory are combined to identify a set of maximal patterns.

The pattern discovery method of the present invention is advantageous because all patterns with a minimum support are reported without enumerating the entire pattern space. This makes our approach efficient. Moreover, the patterns are preferably generated in order of maximality, i.e. the maximal patterns are generated first. As a result, a redundant pattern can be easily detected by comparing it to the patterns already generated. Thus, no costly post-processing or complicated bookkeeping is required.

DETAILED DESCRIPTION OF THE INVENTION

Figure 1:
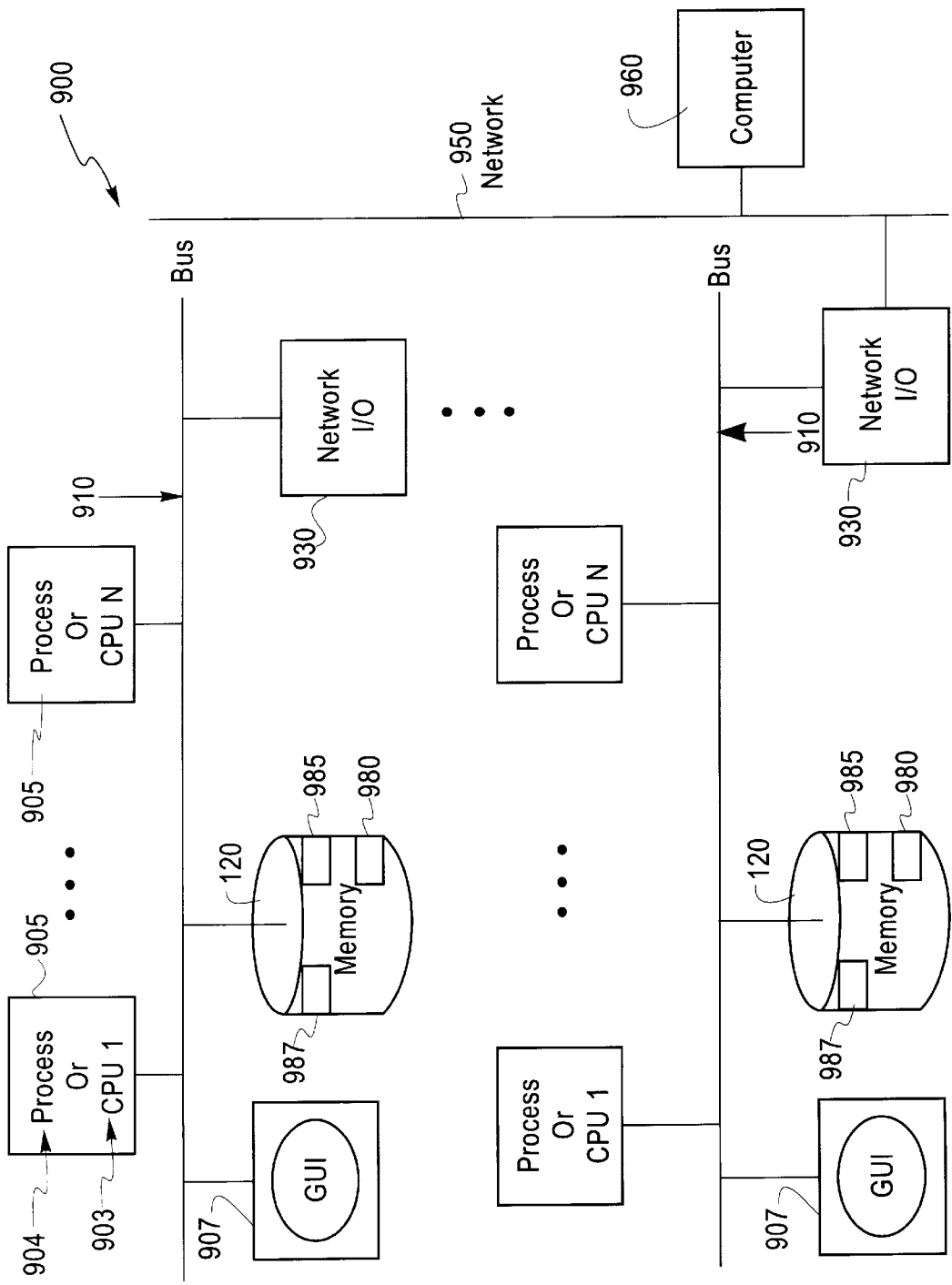
FIG. 1 is a block diagram of a computer processing system wherein the pattern discovery method of the present invention may be embodied.

FIG. 1 is a block diagram of an embodiment of a computer system 900 that is used by the present invention. The system 900 has one or more computers or processes. An example of a computer 905 is a central processing unit (CPU) 903 connected to a bus 910 that is further connected to memory 120, a graphical user interface 907 (such as a display), and optionally a network input/output (I/O) device 930. Memory 120 typically includes persistent storage (such as ROM, a hard disk drive, a CD-ROM drive, an optical drive, ROM or other suitable storage device) and non-persistent storage (such as RAM). The operating system and application programs that execute on the CPU 903 are typically stored in persistent storage and loaded into non-persistent storage for execution by the CPU 903. Portions of the operating system and application programs that execute on the CPU may be loaded from network resources into memory 120 via the network I/O device 930. An example of a such a system 900 is the IBM RS/6000 workstation. The pattern discovery method of the present invention as described below preferably is stored and executed as an application on one or more such computer systems 900.

The pattern discovery method of the present invention described herein is a deterministic one and has the ability when given a set S of event streams in any alphabet $\Sigma$ to discover all the patterns which occur at least twice in the set of event streams. For our purposes, a pattern is defined as any regular expression of the form:

$$\Sigma(\Sigma \cup \text{`.'})\Sigma,$$

where the character '.' (referred to as the don't-care character) is assumed not to be in $\Sigma$.

What this means is that the method will discover anything that appears at least twice (or any user-specified number of times that is greater than 2). By "anything" here we mean that we impose no restriction on the number of characters that will participate in the pattern; furthermore, we impose no restriction on the relative arrangement that the characters will have. In other words, a pattern is defined to be any combination of alphabet characters and "don't care" characters with any spatial extent, which appears at least twice in the input under consideration.

Let us illustrate the above with a specific example utilizing an event stream of 2,000 characters from the English alphabet.

on. If the stream contained N=2000 characters, the minimum length was $l_{min}$=10, and $\Sigma$=26, then ignoring boundary conditions, just for the first iteration would require $N(\Sigma+1)^{lmin} \sim 5.4^{13}$ operations! For the shown stream, the embedded phrase has a length of 34, making such an approach prohibitive.

The pattern discovery algorithm of the present invention can determine the phrase and the locations of the phrase using limited resources. The hidden phrase is "F..A..S.T...AN.D..A.C...C.U.R..A.TE" (where the dots are occupied by characters of the otherwise random stream) and appears a total of five times in the shown stream.

Even knowing that the hidden phrase begins at the locations marked with the circles as depicted in Example 1 above, it is not easy to discover what the phrase is or how long it is.

Although the nature of the method is demonstrated above using a single stream of letters, the method directly extends to the case where the input is a collection of several sequences of letters. Also, the algorithm imposes no restriction on the size of the alphabet that the sequences can be built from.

One of the things contributing to the method's strength is the loose definition of what a pattern is. There is no restriction on the symbol composition of the pattern, its spatial extent, minimum length, maximum length or minimum number of occurrences.

Moreover, the method does not make use of any alignment to discover the patterns. As mentioned above, the use of multiple string alignment as the main tool for discovering patterns is plagued by a number of problems. Domain swapping is one of them: if a, b, and c denote three patterns, it may happen that several of the input sequences will contain the patterns in the order a-b-c, a second set will contain the patterns in the order b-a-c and a third set will contain the patterns in the order c-b-a. Any approach that relies on alignment is bound to perform poorly on such a data set; and this will be particularly true if the three occurring patterns contain only a few characters while at the same time spanning a large portion of the sequence (such patterns are typically referred to as weak patterns).

Another characteristic of the method is that, although it is deterministic, it does not require any search of the corresponding search space; although counterintuitive, such a

```
>example 1
QOJPYBHHLSJUEXDFNYHLDSUXGTDLYHTUBLOCNDCXXIGUYQLQGLYFQJWGFPUTKVRYFNNJQXEQXKJYKAMNONKF)A
OYSGTOLWANADTLAFCIMFCMUPRMRATTEGEZSMZFANOTCTVYDAQPJXMSNQQZKUTFXLDYMXOCIGIZRMCYPKVTVBMN
LXYOHNDRCKFHEVGUQQEHQTQGFCXJDYACDJXKSS(F)AMUSBTJEQANMDICACCLXMCSUARASAGTEXVTVIEZEOAQV(F)
DAFPSITLOKANEDXOAJCWLNCVUBRCSAOTEIBHAUDOPHXFIZNBFMJRRHGYPPZGUNDKKUHJGSBHPIXYLBAXMPLOCG
DVKXTSGSDXDPNZHWIPAZHEDWEVFPJNSNSDBLHXRCJCGJXHTNIQCQKOYFFNKZMPNHGKCVGCBCOOACSQWXJFRDJY
CINMPLUTNSXGKMOBZVKDHTMXXWJGXVJGCYWLDDXLIOPDPBUXEJNBPZDKDPPVYXPHFTHYXRUPCXVVXIQDWMGDTM
WBMBDDXTPCZBXJPWMZJRMKE(F)ADPSKTTSFANCDQXAICHJHCOUHRGBALTEOKCZZXETQMUOKF)AWPSATMWGANED
OIAMCVFMCCUZRWSAJTEBKBYUOEEVPWQXAIXXIESOKKLXJTZUDEUIFSHTHZYFVIFJLPYCLZKYTWRWTAWKYYPNRI
EAARSLIZNWWCFORKISDYYCCESGJTYWPYUWRWUEMLWXZQDLBZVJMIOOSQAIJDETDAHVRFPZKWOAJHALBMSBCMNI
PILEDYEBTXELJJWEFCEGTXGIHMJOOSCKFGIRRRYOOUZNNAJOZDKHLVTTOCYGWVILKQKDLGRSKRMIBUBHETTDDO
TWFGKTYEVNZVTTLCLZBCOKCQDTDPJJSVSZIZQRBFPYOKBCMWSPPAAPQPYJBLAKHWVNPYYPMPFIEKRNXINYIQKC
SZVYQHUWCZSNTFWXXNDNVLILVCRFOYDMRUPOAOPDFCSLVSRCV
```

In this stream, an adversary has hidden a phrase several times and has told us nothing as to the length or the composition of the phrase. The only thing that we have been told is that the phrase was hidden a minimum of two times.

A simple, straightforward approach would be to exhaustively generate first all pattern of length $l_{min}$ and check them against every possible location of the stream, then all patterns of length $l_{min}$+1, all patterns of length $l_{min}$+2, and so thing is possible and contributes to the method's speed. And, of course, in this manner, the method requires no clustering or classification steps.

In order to facilitate description of the pattern discovery method of the present invention, a set of definitions follows.

Consider a finite set of events $\Sigma = \{c_1, c_2, \ldots, c_n\}$. The set $\Sigma$ is called an alphabet and the elements of $\Sigma$ are interchangeably referred to as events or symbols or characters. In what follows, the English alphabet (capital letters) will be used as an example.

Given an alphabet $\Sigma$, we define an event stream over $\Sigma$ to be any member of the set $\Sigma^+$, i.e. any sequence of characters comprising one or more elements of $\Sigma$. For the English alphabet for example, the following are valid strings:

"APPLE", "CONTROVERSY", "AAAFGHRT", "HHHHHHH"

For every event stream s, we use length(s) to denote the length of s. For example, length("APPLE")=5. In the discussion that follows, the term event stream will be used interchangeably with the terms sequence and string.

Given a sequence s and a character c of that string, the offset of c is defined as the character's position within s. For example, if s="APPLE", then the offset of 'A' is 1, the offset of the first 'P' is 2, the offset of the second 'P' is 3 etc. If the offset of c within s is i, we will also call c the i-th character of s and use the notation s[i] to refer to it.

In the following, we will also make use of the term template. A template is a mask that when placed over a sequence of characters identifies those characters that should be considered and those characters that should not be considered. For example, a template may be a string defined over the alphabet $\{$'0', '1'$\}$. To avoid confusion, '0', '1' are assumed to be special characters which do not belong to the alphabet $\Sigma$ under consideration. Given a sequence s, a template t and an offset i within the sequence s, we can obtain a string, which we denote str(s, t, i), by placing t beginning at offset i of s and considering only those characters from the sequence s which are covered by an '1' when the template t is placed over s such that the template's first character coincides with the i-th character of s. For example, consider "ABDOMINAL" to be the sequence s, and "10011" to be the template t. Then, str(s,t,1)=str("ABDOMINAL", "10011", 1)="AOM," sir(s,t, 2)=str("ABDOMINAL", "10011", 2)="BMI," str(s,t,3)=str("ABDOMINAL", "10011", 3)="DIN" etc. For the sake of simplicity, the description of the present invention below utilizes templates that are strings defined over the alphabet $\{$'0', '1'$\}$. However, the present invention is not limited in this respect, and thus can use templates that are defined over any 2 member alphabet consisting of special characters which do not belong to the alphabet under consideration.

A template is said to be proper if it begins and ends with a letter that identifies that the corresponding character of the sequence should be considered (i.e., '1'); a template not satisfying this constraint will be called improper. For example, "0011001" is an example of an improper template, whereas "11000101" is an example of a proper one. A template I is said to be an <i, k> template (i, k∈N, i≤k) if it considers exactly i characters (for the example used here, if it contains exactly i '1's) and its length does not exceed k, i.e. i≤length(t)≤k.

A pattern over $\Sigma$ is defined to be any string over the alphabet $\Sigma \cup \{$'.'$\}$. Again, '.' is assumed to be a special character, not part of $\Sigma$. . We differentiate '.' from the characters of $\Sigma$ by referring to '.' as the "don't care" character (or simply "don't care") while the characters of $\Sigma$ are referred to as the "regular" characters. For our example alphabet, examples of valid patterns include:

"A..LE" "C.NTR...RSY" "..AFG.RT" "H....H." among others.

A pattern is called proper if it begins and ends with a regular character. From the valid patterns listed above, the first two are proper while the last two are not. A pattern can be thought of as being generated by the pair (t, s), where the sequence s is a string over the alphabet $\Sigma$ and the template t contains exactly length(s) many '1's. The pattern that this pair generates is denoted by p(t, s) and can be obtained by replacing the '1's of the template with the respective characters of the sequence and reporting them in the order the characters are encountered in s; the '0's contained in the template are substituted by the don't care character. For example, the pattern "A...PPL.E" is generated by the pair ("100011101", "APPLE").

In a similar manner, given a pattern P, there is a unique template-string pair (t, s) that generates P. For example, if P="D..AR.K" then t="1001101" and s="DARK". We denote the template t and the sequence s generating the pattern P by t(P) and s(P) respectively. Clearly P is a proper pattern if and only if t(P) is a proper template.

A pattern P is said to be an <i, k> pattern (with i≤k) if and only if:

it has at least i regular characters;

every sub-string of P with length k contains at least i regular characters.

Given a sequence s and a pattern P, we will say that the sequence s matches the pattern P at offset i (where 1≤i≤length(s)–length(P)+1) if:

$$\forall j,\ 1 \leq j \leq \text{length}(P) : (P[j]='.') \lor (i\ P[j]=s[i+j-1])$$

In other words, a sequence s will match a pattern P at offset i if and only if every regular character of P agrees with the character of s at the respective offset. For example, the string s="APPLE" matches the pattern "A.PL" at offset 1 ('A'⇔'A', 'P'⇔'.', 'P'⇔'P', 'L'⇔'L'). Similarly, the same string matches the pattern "P.E" at offset 3. A sequence is said to match a pattern if it matches the pattern at one or more offsets.

Let $P_1$ be an arbitrary pattern and consider any pattern $P_2$ obtained from $P_1$ by repeated applications of either of the following operations:

append (to the left or right) a regular or a don't care character.

replace a don't character by a regular character.

Any pattern $P_2$ so obtained is called a sub-pattern of $P_1$. Alternatively, $P_1$ is said to be a super-pattern of $P_2$. For example, if $P_1$="P..KL" then $P_2$="AP..LFO" is a sub-pattern of $P_1$. It can be obtained from $P_1$ by turning 'K' into '.' and appending the characters 'F', 'O' to the right and the character 'A' to the left of $P_1$. Observe that $P_2$ is a restriction of $P_1$, in the sense that any string matching $P_2$ also matches $P_1$. A sub-pattern (respectively super-pattern) is called proper if it is a proper pattern in its own right.

Let P be any proper <i, k> pattern. For any j, where 1≤j≤i, the function prefix(P,j) is defined as returning the minimum length prefix of the pattern p containing exactly j regular characters. By definition, prefix(P,j) returns a pattern which ends with a regular character. Similarly, suffix(P,j) is defined as returning the minimum length suffix of the pattern P containing exactly j regular characters. Clearly, both prefix(P,j) and suffix(P,j) are proper sub-patterns of P.

Let $S=\{s_1, \ldots, s_m\}$ be a set of one or more sequences $s_i$ over an alphabet $\Sigma$. . Given an arbitrary pattern P over $\Sigma$, let $\text{List}_{S(P)}=\{(i, j)\ P\text{ matches } s_i\text{ at position }j\}$. We call this list the offset list of P with respect to S (or simply, the offset list of P when S in unambiguously implied). For convenience, we assume $\text{List}_{S(P)}$ to be ordered according to the usual ordering in N×N: i.e., $(i_1, j_1)$ precedes $(i_2, j_2)$ in the ordering if $(i_1<i_2)$, or $(i_1=i_2)$ and $(j_1<j_2)$. So, the elements of $\text{List}_{S(P)}$ are assumed to be listed according to this order and thus it makes sense to refer to the k-th element of $\text{List}_{S(P)}$. For example, for the set of sequences S={"ALSO", "HALLO"} and the pattern P="L.O" we have that $\text{List}_{S(P)}$=((1, 2), (2, 3)), i.e. the ordered list of all the positions where the strings in S match the pattern.

If P and P' are two patterns, then the offset lists $\text{List}_{S(P)}$ and $\text{List}_{S(P')}$ will be called compatible if:

they have the same cardinality, i.e. $\text{List}_{S(P)}$=$\text{List}_{S(P')}$=l;

∃ an integer h such that ∀k, 1≤k≤l
  if ($i_1, j_1$) is the k-th element of $\text{List}_{S,}$) and ($i_2, j_2$) is the k-th element of $\text{List}_{S(P')}$, then ($i_1$=$i_2$) ∧($j_1$-$j_2$=h).

In other words, the two offset lists will be compatible if and only if the corresponding patterns appear in the exact same sequences and always at a constant displacement h one from the other. This, in practice, means that the two patterns are really pieces of a larger one.

When the integer h in the definition above is known, the lists will be called h-compatible. Notice that, in general, h can be either positive or negative. In the case that it is negative, and without loss of generality, we can simply interchange P and P' so that h becomes positive. In what follows, all h-compatible lists will be assumed to have been given in the order that makes h non-negative.

A pattern P is said to be maximal with respect to a set of sequences S if there exists no other pattern P' such that:

P' is a sub-pattern of P; and, the offset lists of the P and P' are compatible.

The notion of maximality will be discussed at length below. Reporting patterns which are not maximal is typically undesirable. Such patterns are redundant since they are subsumed by other patterns which are less general (and consequently, more descriptive). Reporting non-maximal patterns not only increases the size of the output unnecessarily but it also makes it harder to identify the maximal patterns which are of interest.

Having available the above definitions, the pattern discovery method of the present invention can be used to solve the following problem:

Problem 1

Given a set S={$s_1, s_2, \ldots, s_m$} of one or more sequences $s_i$ over an alphabet Σ of characters, and positive integers L, W and K, find all <L,W> patterns that match K or more of the input sequences in S.

As defined above, every substring of an <L,W> pattern that begins and ends with a regular character and contains exactly L regular characters, has length no more than W.

The pattern discovery method of the present invention proceeds in two phases: sampling and convolution. In the sampling phase, elementary patterns are gathered for the set S. An elementary pattern or sample (the two terms are used interchangeably) preferably is a proper <L,W> pattern with exactly L regular characters. During the convolution phase, elementary patterns are combined into more complex patterns.

The basic conceptual structure used throughout our method is the compound pattern, which is defined simply as a pair U=(U, $\text{List}_{S(U)}$), where U is a pattern and $\text{List}_{S(U)}$ is its offset list with respect to the input set S of sequences. For example consider the set of sequences S={s1="AABC", $s_2$="SDABBB"}. Then the compound pattern corresponding to the pattern "A.B" is simply ("A.B", {(1, 1), (2, 3)})

since the pattern "A.B" appears in the sequences $s_1$ and $s_2$ at the offsets 1 and 3 respectively.

In what follows, patterns will be denoted using italicized upper-case letters, whereas compound patterns will be denoted using normal bold-faced, upper case letters.

Sampling Phase

During the sampling phase, important elementary patterns (samples) are gathered. The notion of importance depends on the particular pattern discovery problem under consideration. For example, for problem 1 as set forth above, a sample is deemed important if it matches at least K of the input sequences.

One skilled in the art will realize that there are many ways to generate the important elementary patterns. The sampling phase may use the recursive, depth-first method outlined in Sagot, Viari and Soldano, "*Multiple Sequence Comparison: A Peptide Matching Approach*", Proceedings Combinatorial Pattern Matching Conference, 1995, pp.366–385, herein incorporated by reference it its entirety. Alternatively, the sampling phase may use templates to generate important elementary patterns.

Figure 2:
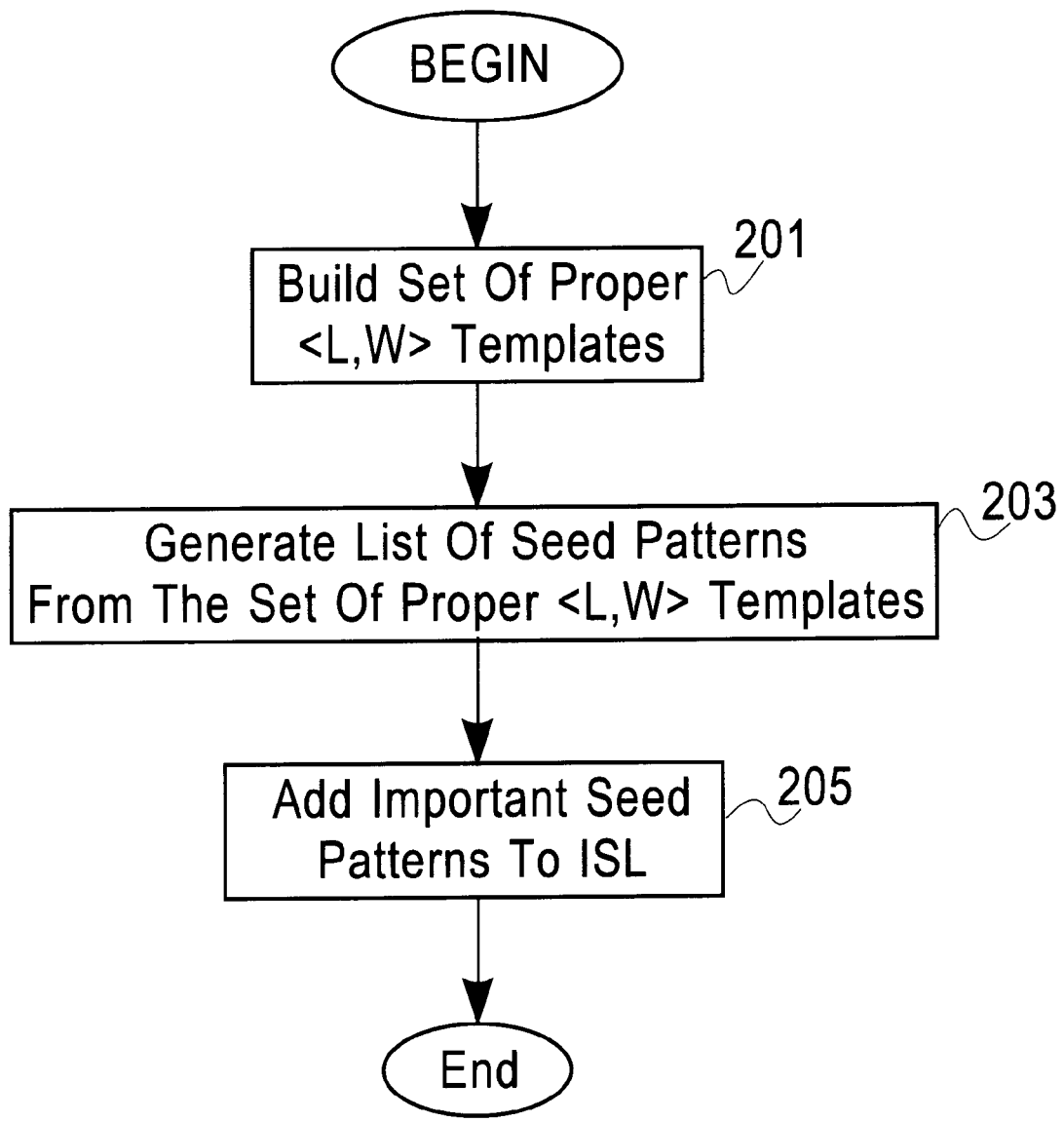
FIG. 2 is a flow chart illustrating an embodiment of the sampling phase of the pattern discovery method of the present invention.

FIG. 2 illustrates an exemplary embodiment that employs templates in the sampling phase. The sampling phase of FIG. 2 begins in step 201 by building a set of templates. Preferably, the set of templates generated in step 201 is the set of proper <L,W> templates. As described above, a <L,W> template contains exactly L "1's" and its length does not exceed W. Moreover, a <L,W> template is proper if it begins and ends with a "1". An example of the sub-steps in generating the set of proper <L,W> templates is discussed below with respect to FIG. 3.

Figure 4:
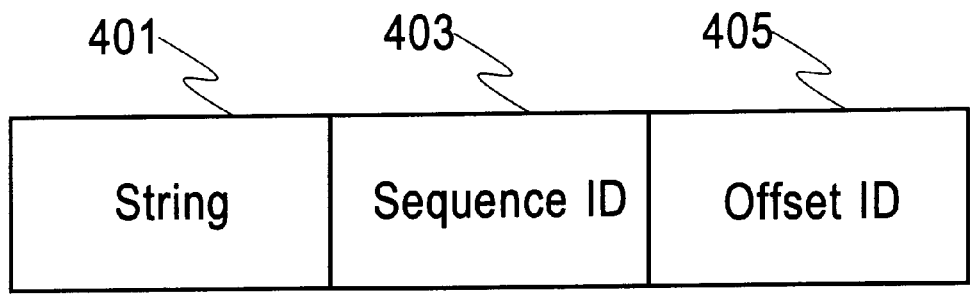
FIG. 4 is a pictorial illustration of an entry in the list of seed patterns generated on step 203 of FIG. 2.

In step 203, a list of seed patterns is generated from the set of templates generated in step 201. The list of seed patterns preferably includes a plurality of entries each associated with a given seed pattern. As shown in FIG. 4, each entry preferably includes a string field 401, one or more sequence ID fields 403 (one shown), and one or more offset ID fields 405 (one shown). The string field 401 contains (or points to) a string u of characters. Each sequence ID field 403 identifies the sequence $s_i$ within the set S where the string u is found. Each offset ID field 405 identifies the offset of the string u in the sequence $s_i$. The sequence ID field 403 and offset ID field 405 may be paired together to form an OffsetList as discussed below. An example of the sub-steps in generating the list of seed patterns is discussed below with respect to FIG. 5.

Figure 6:
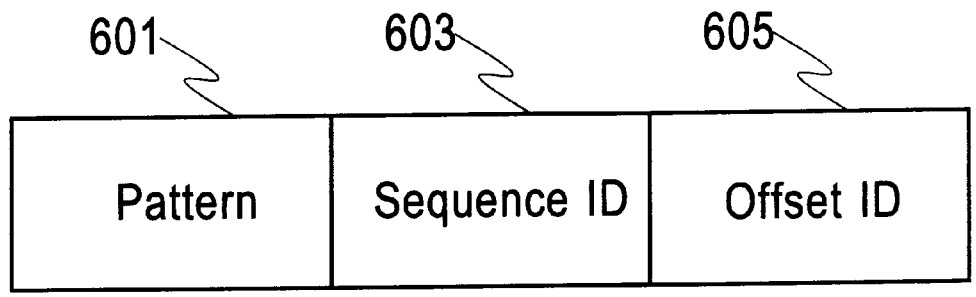
FIG. 6 is a pictorial illustration of an entry in the list of important patterns generated on step 205 of FIG. 2.

Finally, in step 205, one or more seed patterns in the list of seed patterns generated in step 203 is examined to determine if it is "important". As described above, for problem 1, a seed pattern is important if it matches at least K characters of the input sequence S. If the seed pattern is deemed "important", the seed pattern is added to a list of important patterns (ISL). The ISL preferably includes a plurality of entries each associated with a given important pattern. As shown in FIG. 6, each entry preferably includes a pattern field 601, one or more sequence ID fields 603 (one shown), and one or more offset ID fields 605 (one shown). The pattern field 601 contains (or points to) a pattern. Each sequence ID field 603 identifies the sequence si within the set S where the pattern is found. Each offset ID field 605 identifies the offset of the pattern in the sequence $s_i$. The sequence ID field 603 and offset ID field 605 may be paired together to form an OffsetList as discussed below.

Figure 3A:
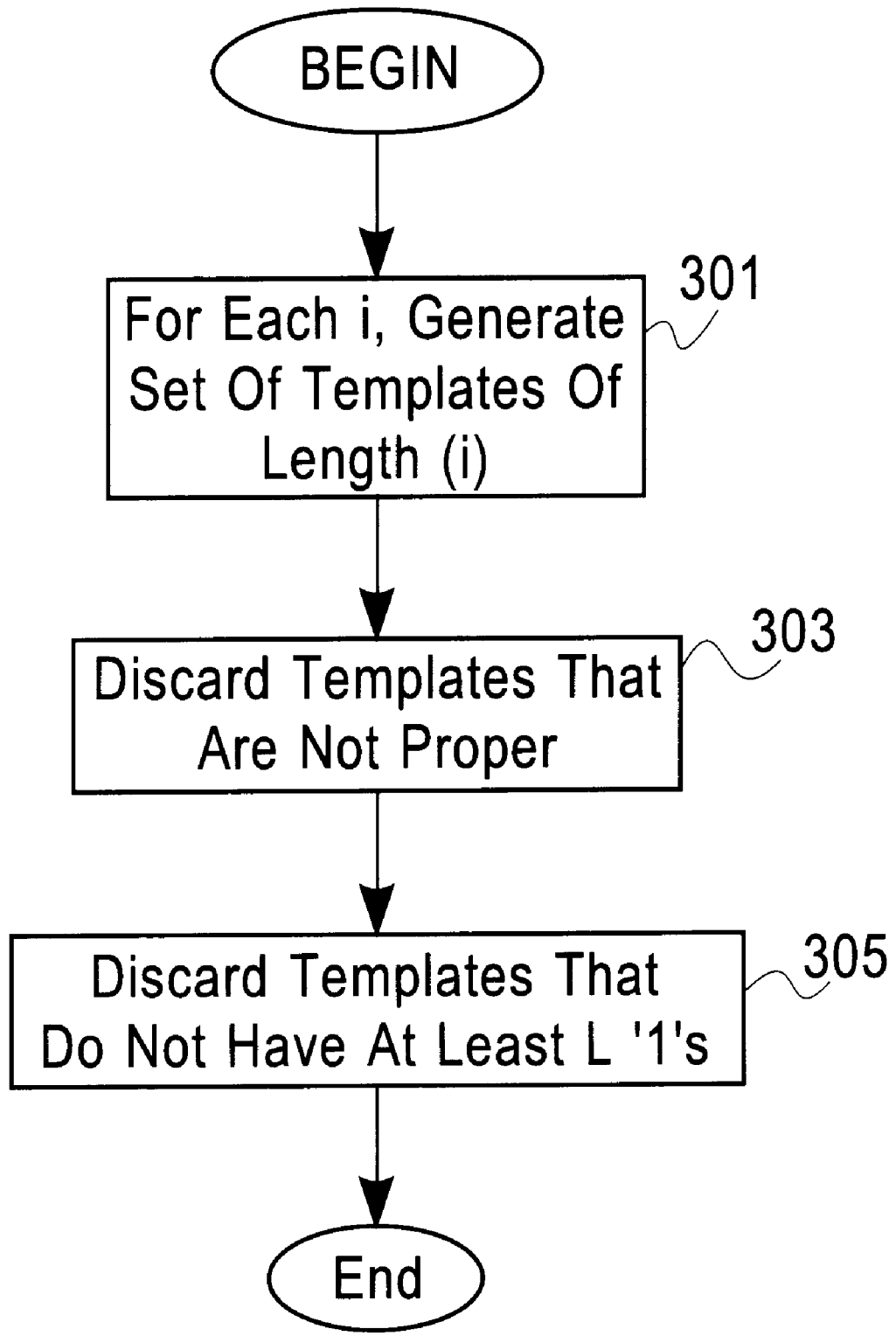
FIGS. 3(A)–(C) illustrate examples of the steps for generating the set of proper templates of step 201 of FIG. 2.

Referring to FIG. 3A, the set of proper <L,W> templates may be generated by first performing step 301 wherein, for each integer i in the interval L≤i≤W, the set of templates having a length i is generated. For example, consider a case where L=3 and W=4, the set of templates generated in step 301 would include:

i=3
  {000}, {001}, {010}, {011}, {100}, {101}, {110}, {111} i=4
{0000}, {0001}, {0010}, {0011}, {0100}, {0101}, {0110}, {0111}, {1000}, {1001}, {1010}, {1011}, {1100}, {1101}, {1110}, {1111}

In step 303, templates that are not proper (i.e., do not begin and end with a '1'} are discarded from the set of templates generated in step 301. Thus, in the example set forth above, the following templates would remain:

{101}, {111}, {1001}, {1011}, {1101}, {1111}

Finally, in step 305, templates that do not have at least L 1's are discarded and the operation ends. Thus, in the example, the following templates would remain:

{111}, {1011}, {1101}, {1111}

Figure 3B:
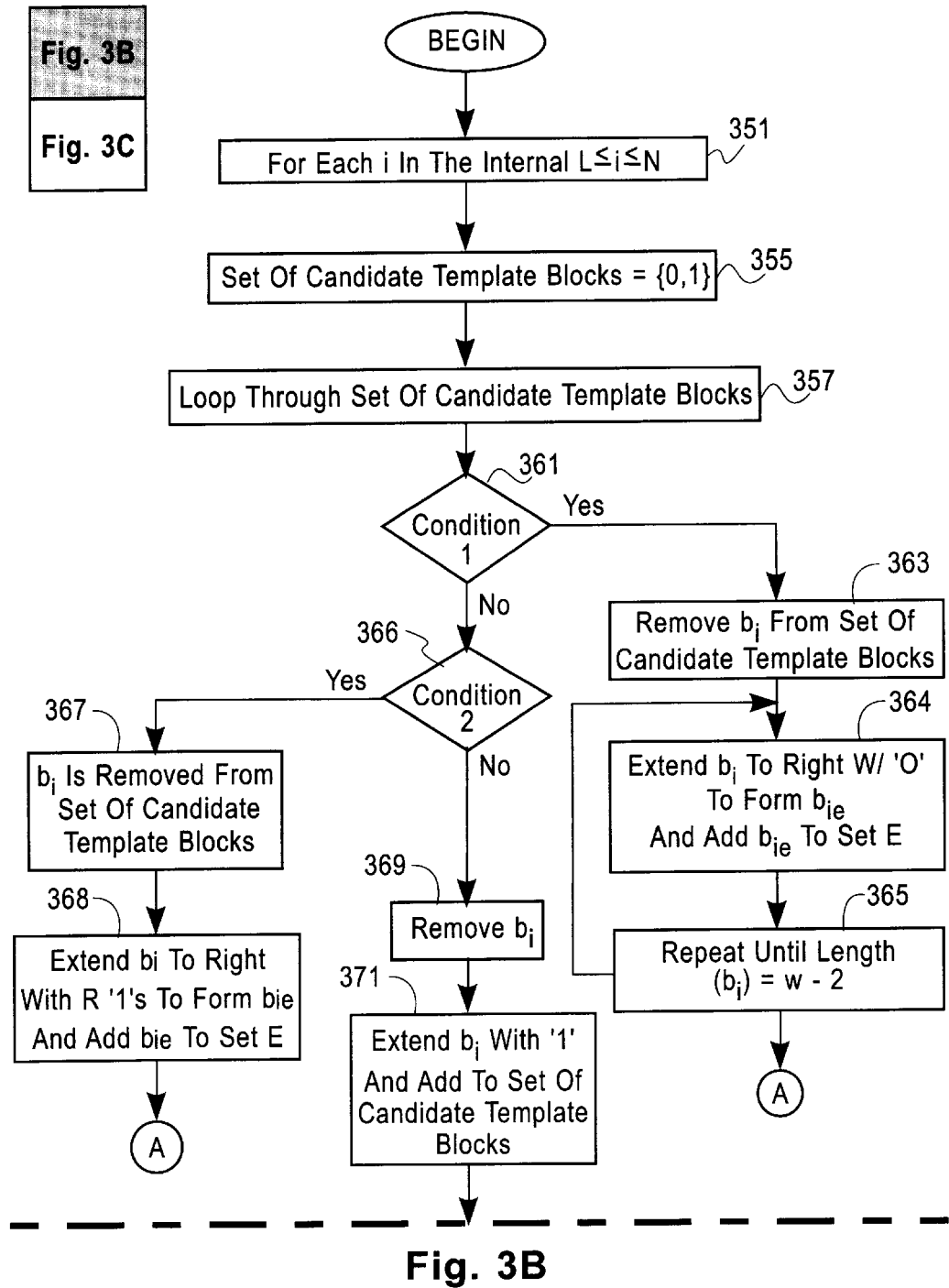
Figure 3C:
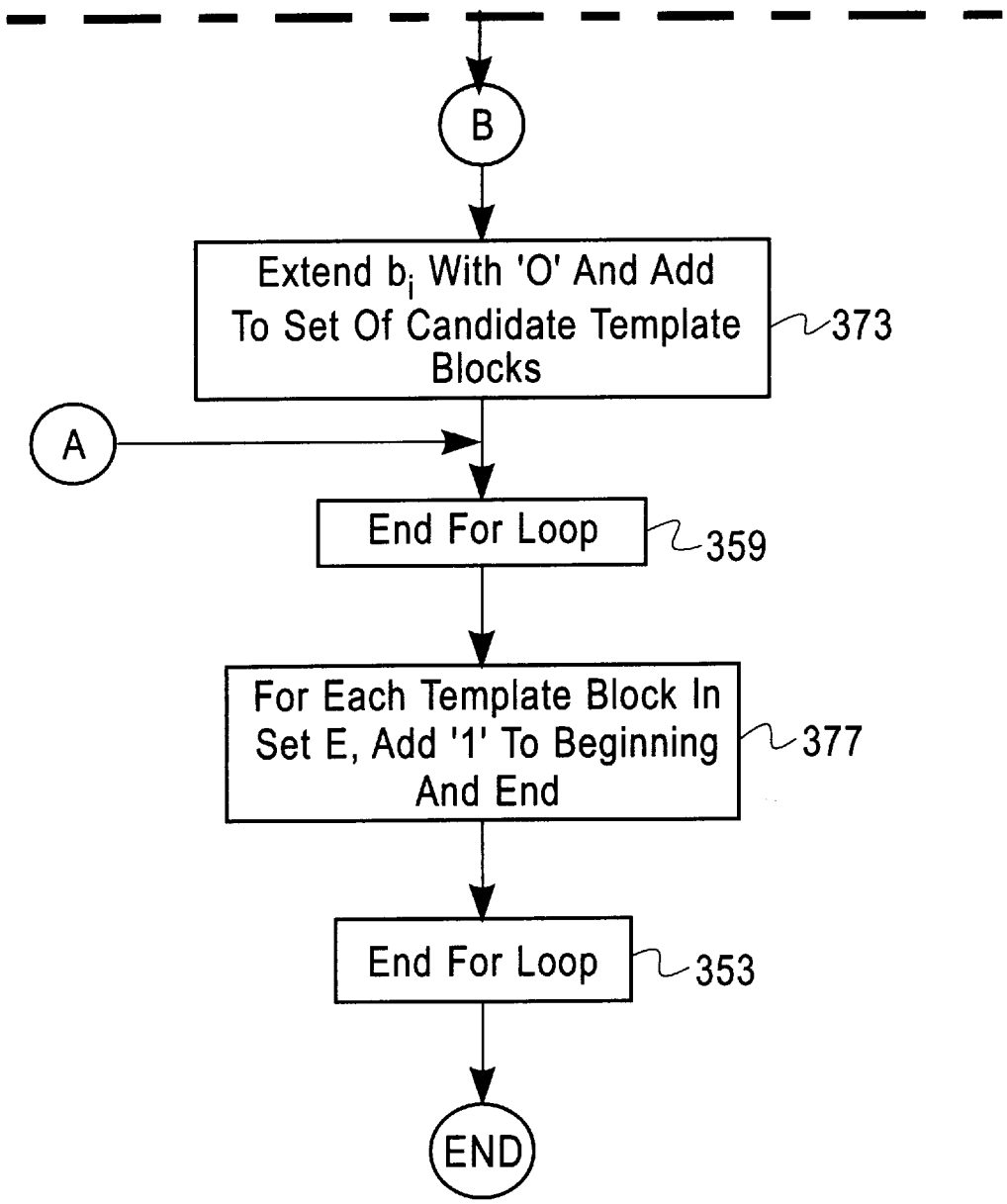

FIG. 3B illustrates an alternate method for generating the set of proper <L,W> templates. This method takes advantage of the fact that a proper <L,W> template begins and ends with a '1'. The method performs a loop 351–353 over each i in the interval $L \leq i \leq W$ to build the set of proper templates of length i. In step 355, a set of candidate template blocks is initialized to {'0', '1'}. In step 357–359, operation loops through the set of candidate template blocks. In step 361, it is determined whether the following condition is satisfied with respect to a given candidate template block $b_i$:

the number of '1's in $b_i$=(L−2).

If the condition in step 361 is satisfied, operation continues to step 363 wherein $b_i$ is removed from the set of candidate template blocks, $b_i$ is extended to the right with a '0' to form an extended candidate template block $b_{ie}$, and the resulting extended candidate template block $b_{ie}$ is added to a set E ot template blocks. The step of extending the candidate template block and adding the resultant extended candidate template block to set E (i.e., extending the extended candidate template block $b_{ie}$ with a '0' and adding the result to set E) is repeated until the length of candidate template block is equal to (W−2) and operation then returns to step 357 to process the next candidate template block in the set of candidate template blocks. If the condition in step 361 is not satisfied, then operation continues to step 365.

In step 365, it is determined whether the following condition is satisfied:

((W−2)-length of $b_i$)=((L−2)-# of '1's in $b_i$)

If the condition in step 365 is satisfied, then operation continues to step 367 wherein $b_i$ is removed from the set of candidate template blocks, be is extended to the right with R number of '1's (where R=(L−2)−# of '1's in $b_i$) to form an extended candidate template block $b_{ie}$, the resulting extended candidate template block $b_{ie}$ is added to a set E of candidate template blocks, and operation returns to step 357 to process the next candidate template block in the set of candidate template blocks. If the condition in step 365 is not satisfied, then operation continues to steps 369 through 375.

In step 369, $b_i$ is removed from set of candidate template blocks. In step 371, $b_i$ is extended with a '1' and added to set of candidate template blocks. In step 373, $b_i$ is extended with a '0' and added to the set of candidate template blocks. Finally, in step 375 operation returns to step 357 to loop through set of candidate template blocks.

When the set of candidate template block is empty, loop 357–359 terminates and operation continues to step 377 wherein, for each template block in the set E, a '1' is added to the beginning and end of the template block to form the set of proper <L,W> templates. Thus, in the example presented above, the following templates would be formed:

{1011}, {1101}, {1111}

One skilled in the art will recognize that the steps presented above with respect to FIGS. 3(A) and (B) are exemplary, and that there are many other ways of generating the set of proper <L,W> templates.

Figure 5:
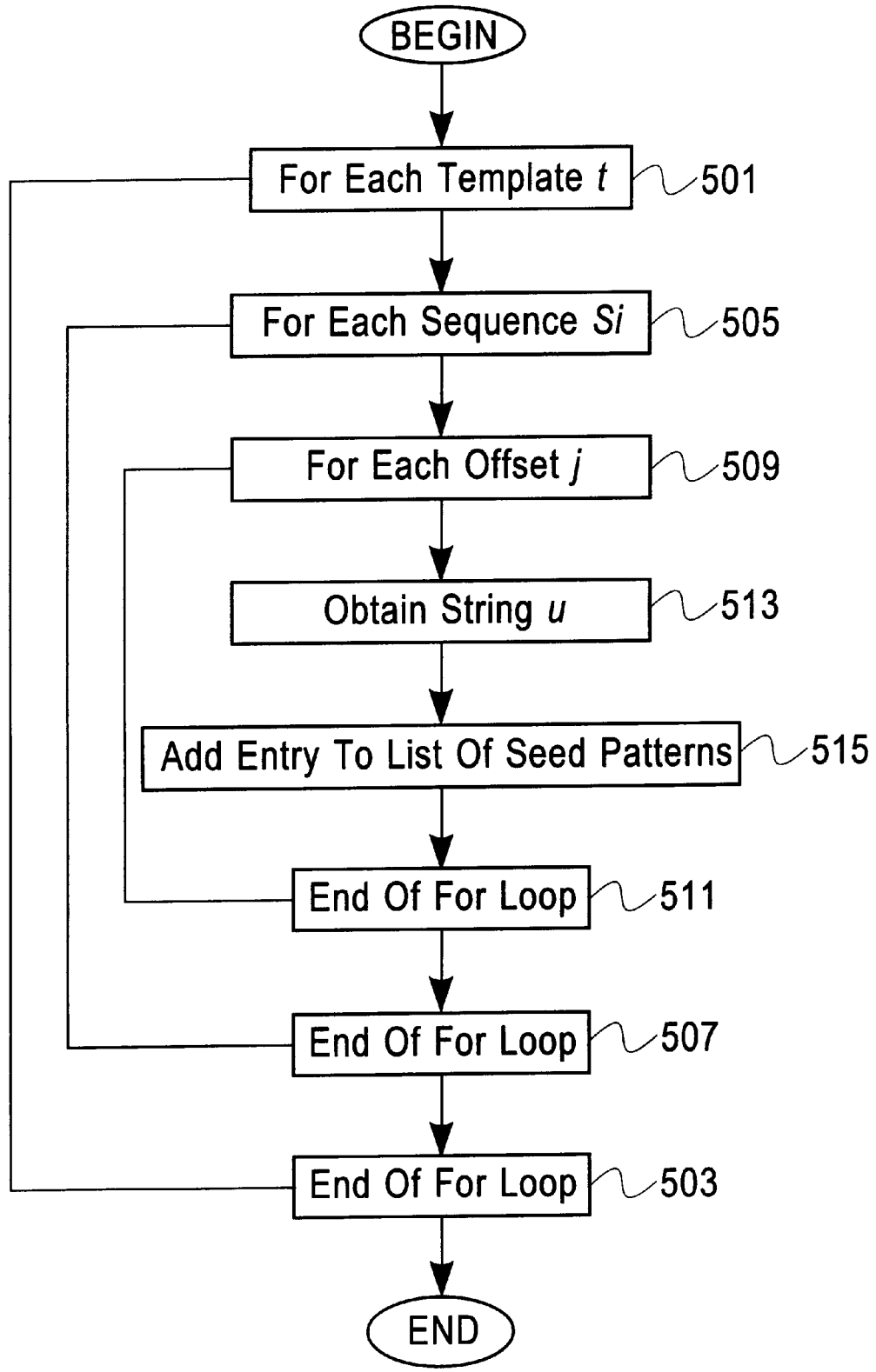
FIG. 5 illustrates an example of the steps for generating the list of seed patterns of step 203 of FIG. 2.
Figure 7:
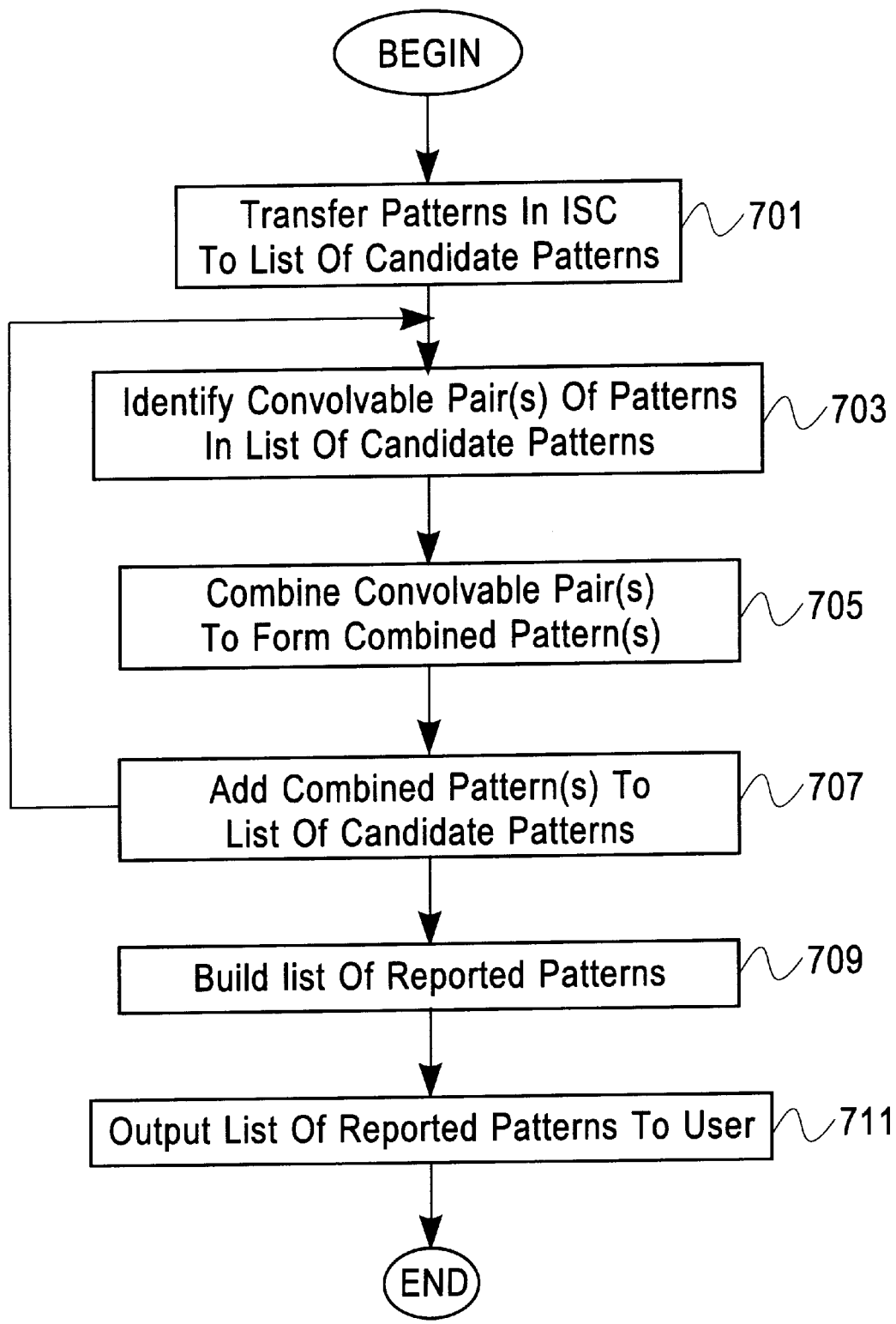
FIG. 7 is a flow chart illustrating the convolution phase of the pattern discovery method of the present invention.

Referring to FIG. 5, the list of seed patterns may be generated by performing a 3-part nested loop as follows. First, a loop 501–503 is performed over each template t in the set of templates generated in step 201. Second, for each template t, a loop 505–507 is performed over each sequence s, in the set S. Third, for each template t and each sequence $s_i$, a loop 509–511 is performed over each offset j in the given sequence $s_i$. Steps 513 and 515 are performed within the inner loop 509–511 of the nested loop. In step 513, a string u=str($s_i$, t, j) is obtained by placing the template t at the offset j of the sequence $s_i$. In step 515, the list of seed patterns is updated with an entry as shown in FIG. 4 that includes:

a string field 401 that contains (or points to) the string u;

a sequence ID field 403 that identifies the sequence $s_i$; preferably, the integer i is stored in the sequence ID field 403; and an offset ID field 405 that identifies the offset j; preferably, the integer j is stored in the offset ID field 405.

As described above, loop 501–503 loops over each template t in the set of templates generated in step 201. However, one skilled in the art should realize that loop 501–503 may loop through any subset of the set of templates generated in step 201. Similarly, as described above, loop 505–507 loops over each sequence $s_i$ in the set S. However, one skilled in the art should realize that loop 505–507 may loop through any subset of the sequences in the set S. Similarly, as described above, loop 509–511 loops over each offset j in a given sequence $s_i$. However, one skilled in the art should realize that loop 509–511 may loop through any subset of the offsets in the sequence $s_i$.

The sampling phase preferably uses a data structure to store compound seed patterns over the alphabet Σ. As defined above, a compound pattern is defined simply as a pair U=(U, $List_{S(U)}$), where U is a pattern and $List_{S(U)}$ is its offset list with respect to the input set S of sequences. This structure will be called Dir (for "directory"). This data structure preferably supports the operations of insertion and member. The insertion operation takes as argument a compound pattern and places in its appropriate position within Dir. The member operation takes as argument a compound pattern and searches Dir to see if that compound patterns is already stored in Dir, in which case it returns a pointer to the place within Dir where that particular compound pattern resides; otherwise it returns an indication that the pattern is not in Dir. There are a a multitude of data structures that can be used for Dir. For example, one plausible solution is a balanced binary search tree (e.g. a red-black tree). However, the choice of data structure is not relevant for the purposes of the description of the method.

Every entry in Dir preferably is of the form (u, OffsetListu) where u is a string of L many characters and $OffsetList_u$ is a list of offsets, i.e. pairs of the form (i,j) where i identifies the i-th input sequence and j an offset within that sequence.

An example of sampling phase is provided in the following pseudo-code:

```
- Generate the set T(L, W) of all proper <L, W> templates.
- for each t ε T(L, W) do
-     Clear Dir
-     for each s_i ε S do
-         for each offset j in s_i do
```

-continued

```
    let u = str(s_i, t, j).
    if (u, OffsetList_u) ∈Dir then
        Add the pair (i, j) the list OffsetList_u
    else
        Create an entry (u, OffsetList_u =
        (i, j)) and insert it in Dir
    endif
    end-for
end-for for every entry (u, OffsetList_u) in Dir do
    V = p(t, u)
    if V is important then
        add (V, OffsetList_u) in the list ISL
        of the important samples
    end-if
end-for
```

In the example, the list of seed patterns is generated as follows. For each proper template t contained in the set T(L,W), for each sequence $s_i$ in the input set S, and for each offset j in $s_i$:

- a string $u=\text{str}(s_i, t, j)$ is obtained by placing the template t at the offset j of the sequence $s_i$;
- if an entry (u, OffsetList$_u$) is already in Dir, then add the pair (i,j) to OffsetList$_u$ to show that the sequence $s_i$ also contains the string U beginning at offset j (when template t is used); otherwise, create an entry (u, OffsetList$_u$), initialize OffsetList$_u$ to (i, j) and insert the entry in Dir.

Moreover, the ISL is preferably generated as follows. After all sequences $s_i$ and offsets j have been exhausted for a given proper template t and the seed patterns corresponding to the given proper template t have been added to Dir, a loop is performed for each entry (u, OffsetList$_u$) in Dir. In this loop, the pattern V=p(t, u) is generated. V is the pattern generated by the template-string pair (t, u), where t is the proper template under consideration and u is the string from the Dir entry under consideration. The pattern V is then examined to determine if the pattern V is "important." For problem 1, the pattern V preferably is deemed "important" if the pattern V matches at least K of the string U under consideration (in other words, if the list OffsetList$_u$ contains offsets from at least K distinct input sequences). If the pattern V is deemed "important", then the pair (V, OffsetList$_u$) is an entry in ISL. Thus, at the end of the sampling phase, the ISL stores all the pairs (V, L) where V is an important sample and L=List$_{S(V)}$. is the offset list of the pattern V with respect to the input set S.

Convolution Phase

In the convolution phase, the important patterns stored in the ISL during the sampling phase are combined into larger and more complex patterns. Before proceeding, we formally define below the operation of convolution. This operation is at the heart of our algorithm and describes a way of combining two patterns into a larger one. By identifying patterns that can be convolved and performing the convolutions in the appropriate order we are able to generate all maximal patterns without enumerating the entire pattern space.

Let PP={P P is a proper pattern). If R is any positive integer larger than 2, then $\oplus_R$ will denote a binary operator which takes two member patterns, P and Q, from the set PP as operands and produces a new pattern (P $\oplus_R$ Q) in the following way:

$$P \oplus_R Q = \begin{cases} \emptyset & \text{if suffix}(P, R) \neq \text{prefix}(Q, R) \text{ or } R > \min\{rc(P), rc(Q)\} \\ PQ' & \text{otherwise} \end{cases}$$

where ∅ is the empty pattern, rc(P) denotes the number of regular characters in the pattern P (and rc(Q) similarly in Q) and Q' is what remains of Q after the prefix prefix(Q, R) is thrown away, i.e. Q=prefix(Q, R) Q'

Given the operator $\oplus_R$, the two patterns P and Q are said to be convolvable if the result of the operation (P $\oplus_R$ Q) is non-empty.

The binary operator $\oplus_R$ can also be applied to compound patterns CPP={(P, List$_{S(P)}$) P belongs to PP } as follows:

$$(P, \text{List}_{S(P)}) \oplus_R (Q, \text{List}_{S(Q)}) = (P \oplus_R Q, L_P)$$

where $L_P$ is empty if P $\oplus_R$ Q=∅ and otherwise $L_P$ will be the maximum-length sublist of List$_{S(P)}$ such that there exists a sublist $L_Q$ of List$_{S(Q)}$ which is (length(P)–length(suffix(P, R)))-compatible with $L_P$. Note that $L_P$ could be empty even if the pattern P $\oplus_R$ Q is not empty. Consider an example where L=3 and an set S contains the following four sequences {$s_1$="HALLO ", $s_2$="HALDRI", $s_3$="SHALPO", $s_4$="FALOO"}. Consider the patterns P="HAL" and Q="AL.O " with their corresponding offset lists: List$_{S(P)}$=((1, 1), (2, 1), (3, 2)) and List$_{S(Q)}$=((1, 2), (3, 3), (4, 2)). Then applying the operator $\oplus_{(L-1)}$ to P and Q we have: P $\oplus_{(L-1)}$ Q="HAL. O" and (P, List$_{S(P)}$)$\oplus_{(L-1)}$=(Q,List$_{S(Q)}$)=("HAL.O", ((1, 1), (3, 2))).

The convolution phase begins in step 701 by transferring the patterns stored in the ISL to a list of candidate patterns. In step 703, one or more pairs of convolvable patterns stored in the list of candidate patterns is identified. In step 705, one or more of such pairs are combined to form a set of combined patterns. In step 707, the set of combined patterns is preferably added to the list of candidate patterns and operation returns back to step 703. In step 709, one or more patterns in the list of candidate patterns may be added to a list of reported patterns. Preferably, a pattern is added to the list of reported patterns only if it is maximal. Finally, in step 711, the list of reported patterns is communicated to a user via an I/O device such as the display or printer.

The convolution stage of the present invention preferably identifies appropriate pairs of patterns P and Q that can be convolved under the operator $\oplus_R$ where R=(L–1). As set forth above, L is a parameter provided as part of the input to the algorithm. One skilled in the art will realize that the present invention is not limited in this respect, and may be utilized with other R values. After such a pair of convolvable patterns has been identified, it is subsequently expanded by convolving the respective compound patterns.

As explained below in more detail, the ordering for which the convolutions occur may be set such that maximal patterns are generated first (i.e., maximal patterns are generated before non-maximal patterns). In this manner, redundant non-maximal patterns may be identified easily by just comparing them to the maximal patterns already generated.

Figure 8:
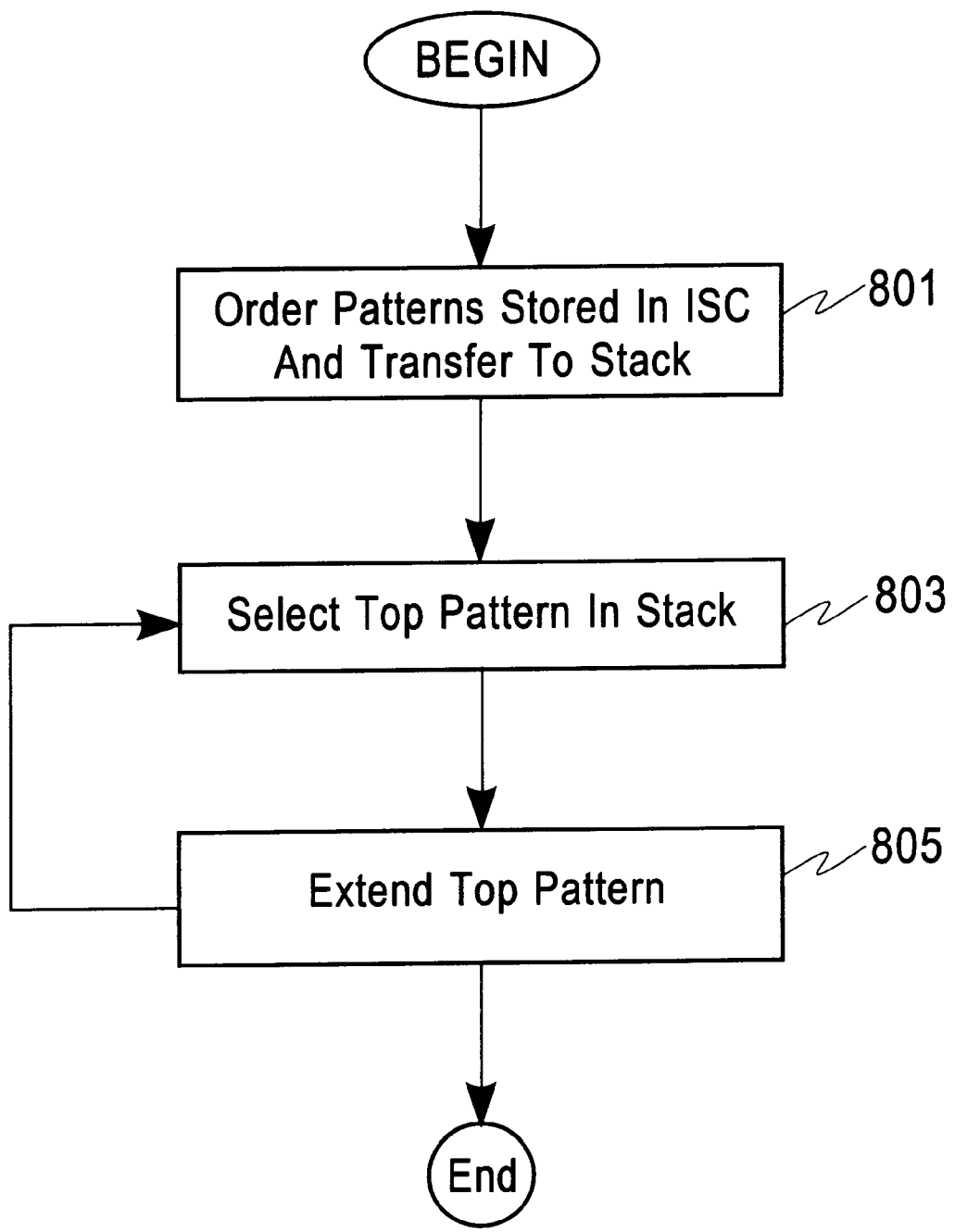
FIG. 8 is a flow chart illustrating the convolution phase of the pattern discovery method of the present invention wherein maximal patterns are generated prior to non-maximal patterns.

An example of the processing of the convolution stage wherein maximal patterns are generated before non-maximal patterns is illustrated in FIG. 8. The operation begins in step 801 by ordering the patterns stored in the ISL and transferring the ordered list of patterns to a data structure supporting last-in first-out (LIFO) functionality, such as a stack, ordered queue, heap, or tree (hereinafter referred to as a stack). In step 803, the top pattern of the stack is selected. In step 805, it is determined if the pattern selected in step 803 can be combined with patterns stored in the stack. More specifically, in step 805, the set of patterns stored in the stack that are convolvable with the pattern selected in step 803 are identified and ordered based upon a predetermined ordering scheme. Preferably, the ordering scheme provides for convolution of patterns that results in non-redundant combinations. If the set of ordered patterns is not empty, one of the patterns in the set may be convolved with the pattern selected in step 803 to create a combined pattern. The selection of the pattern for convolution is preferably based upon a predetermined criterion, examples of which are set forth below. The combined pattern is then placed on the top of the stack and the process returns to step 803. If the set of ordered patterns is empty or there is no pattern in the set selected for convolution, the pattern at the top of the stack is selected as candidate for the list of reported patterns, the pattern is removed from the stack. The processing then returns to step 803. If the stack is empty in step 803, the convolution phase ends. Preferably, the candidate pattern is added to the list of reported patterns only if it is maximal. At the end of the convolution phase, the list of reported patterns is a complete list of maximal patterns that cannot be combined with any other pattern(s)

There are a number of questions arising when one looks at the problem of convolving the samples of ISL. Some of these have to do with efficiency (how to perform the required task without abusing memory and computation time). For example, assume that two compound patterns $P=(P, \text{List}_{S(P)})$ and $Q=(Q, \text{List}_{S(Q)})$ are convolved into the new compound pattern $R=P \oplus_{(L-1)} Q=(R, \text{List}_{S(R)})$. Space will be needed for the representation of the offset list $\text{List}_{S(R)}$. Since $\text{List}_{S(R)}$ is a sub-list of $\text{List}_{S(P)}$, a viable and economical solution could be to just remove this sublist from P and give it to R. Unfortunately this approach is not correct because P might need some of the offsets in $\text{List}_{S(R)}$ for another convolution in the future. So, it seems that new space must be acquired to be used by the offset list of R. Given this, the simple minded convolution approach of "all-against-all" can be extremely insufficient: doing this generates many useless patterns with offset lists that unnecessarily consume large amounts of memory. And not only that: since a new pattern is not immediately reported but has to stay around and try to further convolve (so that the maximal patterns are found) maintaining redundant patterns can also lead to an explosion of the computation time needed for the convolution process.

Given the efficiency requirement mentioned above, the next question to consider is the appropriate order to convolve the patterns in so that the generation of redundant intermediate patterns is avoided (or kept to a minimum). Consider for example the input sequence set S={s1= "ABCDEF", s2="ABCDEG"} and assume that we are looking for patterns appearing in at least 2 sequences. One such pattern is the pattern "ABCDE". Assuming L=3, the following are samples that will be found in ISL after the sampling phase: $P_1$="ABC", $P_2$="BCD", P3="BC.E", P4="CDE". At some point, the pattern $P_1$ will need to be expanded. Both $P_2$ and $P_3$ are candidates for convolution with $P_1$ since suffix($P_1$, L−1)=prefix($P_2$, L−1)=pref($P_3$,, L−1)="BC". The appropriate order is first to convolve $P_1$ with $P_2$ and then the outcome of this convolution with $P_4$. If, instead, $P_1$ and $P_3$ are convolved first then the resulting pattern "ABC.E"is not maximal (neither a useful intermediate step as $P_1 \oplus_{(L-1)} P_2=$ "ABCD" is). So, some rule is needed to decide which pairs of patterns should be convolved. There are also many other efficiency and correctness issues that need to be considered. The convolution process described below addresses all of them.

Before proceeding, two partial orderings on the set of all possible patterns are introduced. These orderings will be used when deciding which pairs of patterns must be convolved so that generating redundant patterns is avoided. It should be noted that the orderings presented below are exemplary, and other orderings may be used by the present invention.

The first ordering classifies the patterns according to their prefixes. The second one does exactly the same thing, but now using the suffixes of the patterns. More specifically, let P[1 . . . n] and Q[1 . . . m] be two arbitrary patterns of length $i_1$ and m respectively (n,m $\geq$0; a length zero pattern is just the empty string). We say that P is prefix-wise less than Q and write $P \leq_{pf} Q$ if n=0 (i.e. P is the empty pattern) and Q[1]='.' or P[1] '.' and Q[1]='.' or P[1], Q[1] are both '.' or both non-'.' and $P[2 \ldots n] \leq_{pf} Q[2 \ldots m]$.

Another way to describe the "$\leq_{pf}$" predicate is the following (we only define the predicate for proper patterns, since this is the only kind of pattern used): consider any proper pattern P. Structurally, P consists of one or more blocks of regular characters with every pair of consecutive blocks being separated by one or more don't cares. For example, the pattern P="AS..SDF.G" has three blocks, namely "AS", "SDF" and "G". The first two blocks are separated by two don't cares while the last two blocks are separated by a single don't care character. A proper pattern P with k blocks can then be represented by the tuple $$(n_1, m_1, n_2, m_2, \ldots, m_{(k-1)}, n_k)$$

where $n_i$ is the length of the i-th block and $m_i$ is the number of don't cares separating the i-th and the (i+1)-th blocks.

For example, the tuple representation for P="AS..SDF.G" is (2, 2, 3, 1, 1). Consider now any pair of proper patterns P, Q and their respective tuple representations $$(n_1, m_1, n_2, m_2, \ldots, m_{(k-1)}, n_k)$$

and $$(2_1, s_1, r_2, s_2, \ldots, s_{(l-1)}, r_l)$$

We say that $p \leq_{pf} q$ if there exists an index i such that one of the following two things happen:

$(\forall j<i: n_j=r_j \forall m_j=s_j) \forall n_i>r_i$ $(\forall j<i: n_j=r_j \forall m_j=s_j) \forall n_i=r_i \forall m_{i+1}<s_{i+1}$ The second of the two partial orderings can be defined using the definition of "$\leq_{pf}$". More specifically, given two patterns P, Q we say that P is suffix-wise less than Q and write $P \leq_{sf} Q$ if $P^R \leq_{pf} Q^R$, i.e. if the reverse of the pattern P is prefix-wise less than the reverse of the pattern Q (the notion of reverse is defined in the standard way; e.g. if P="A..DF.H" then $p^R$="H.FD..A").

The above orderings are preferably used in step 805 of the convolution phase when considering which pattern to convolve with the pattern P currently under consideration. First, we only need to look at patterns Q that are convolvable with P under $\oplus_{(L-1)}$ (i.e. at patterns Q such that suffix(P, L−1)= prefix(Q, L−1). If there are more than one such patterns, such patterns are traversed by first selecting a minimal pattern according to the "$\leq_{pf}$" relation defined above, and then selecting the next minimal pattern according to the "$\leq_{pf}$" relation. Reconsidering the example given at the beginning of this subsection, the patterns that are convolvable with $P_1$="ABC" are the patterns $P_2$="BCD" and $P_3$="BC.E". Since $P_2 \leq_{pf} P_3$, $P_1$ should be convolved with $P_2$ first (which is the correct thing to do).

More specifically, in step 805 patterns are preferably generated in stages. First, all patterns that have offset lists of a maximum length are generated, then all patterns with offset lists of the immediately smaller size and so on. As described above, a stack contains the compound pattern that is being currently convolved. Call this stack Cstack. In order to be able to generate maximal patterns, the entries of C(Stack must be ordered according to the partial order defined above. This means that if $P \leq_{pf} Q$ the compound entry for P must be closer to the top of stack than the compound entry for Q.

We also need two searchable structures that can store entries of the form (U, $CPL_U$) where U is a proper <L–1, W> pattern with exactly (L–1) regular characters and $CPL_U$ is an ordered list of compound patterns. Call these two structures SuffDir and PrefDir. The list $CPL_U$ of an entry (U, ($CPL_U$)) in PrefDir contains all the compound patterns (P, $List_{S(P)}$) $\epsilon$CStack with the property: prefix(P, L–1)=U. In an analogous way, the list $CPL_U$ of an entry (U, $CPL_U$) in SuffDir contains all the compound patterns (P, $List_{S(P)}$) $\epsilon$CStack with the property: suffix(P, L–1)=U.

Furthermore, for every entry (U, $CPL_U$) in either the SuffDir or the PrefDir, the list $CPL_U$ is ordered. More specifically, consider a particular entry (U, $CPL_U$) $\epsilon$PrefDir and two compound patterns P=(P, $List_{S(P)}$) and Q=(Q, $List_{S(Q)}$) both belonging to $CPL_U$. Then if $P \leq_{pf} Q$, the compound pattern P is listed before the compound pattern Q in $CPL_U$. If, on the other hand, (U, $CPL_U$) $\epsilon$SuffDir, then P is listed before Q if $P \leq_{sf} Q$. When we extend the pattern at the top of CStack the appropriate $CPL_U$ list of some entry in either PrefDir or SuffDir is traversed. By having the $CPL_U$ lists ordered as described, we can guarantee that the convolutions are performed in the appropriate order.

Preferably, the convolution phase selects the compound pattern P=(P, $List_{S(P)}$) at the top of Cstack for extension. First, it will extend the pattern to the "right" (suffix-wise) by looking to compound patterns which are convolvable with P (i.e. compound patterns Q=(Q, $List_{S(Q)}$) with the property that prefix(Q, L–1)–suffix(P, L–1)=U. All such patterns can be located by looking at the list $CPL_U$ of the entry (U, $CPL_U$) in PrefDir. Every element Q of the list is visited in order and the convolution R=P$\oplus_{(L-1)}$Q is tried out. If any such R has an offset list long enough to qualify as important (for the current version of the problem in hand) then the new compound pattern R is placed at the top of CStack, thus becoming the new current pattern. After extension in the suffix direction is completed, the same procedure is applied extending the pattern to the left (prefix-wise), now looking for convolvable patterns in SuffDir. When extension in both direction has been completed, the resulting pattern is checked for maximality and if found to be maximal it it added to the list of reported patterns.

```
- sort the samples P = (P, ListS(P)) in ISL in descending order according to their support
- max_seq = max{ support(P) : (P, List_S(P)) ∈ ISL }
- for each i = max_seq downto K do
-     for all P = (P, ListS(P))∈ ISL such that support(P) ≥ i do
-         push P CStack
-     end-for
-     Sort the entries in Cstack according to the ≤_pf relation
-     while CStack is not empty do
new_current_pattern:
-         P = (P, List_S(P)) = pop Cstack
-         U = suffix(P, L-1)
-         if there exists an entry ((U, CPL_U) ∈ PrefDir then
-             while exists Q ∈CPL_U that has not been convolved with P do
-                 Q = next element of CPL_U that has not been convolved with P
-                 R = (R, ListS(R)) = P ⊕_(L-1) Q
-                 if R is important then
-                     push R on Cstack
-                     Locate (prefix(R, L-1), CPL') in PrefDir and insert R in CPL'
-                     Locate (suffix(R, L-1), CPL") in SuffDir and insert R in CPL"
-                     goto new_current_pattern
-                 end-if
-             end-while
-         end-if
-
-         U = pref(P, L-1)
-         if there exists an entry (U, CPL_U) ∈SuffDir then
-             while exists Q ∈ CPL_U that has not been convolved with P do
-                 Q = next element of CPL_U that has not been convolved with P
-                 R = (R, ListS(R)) = Q ⊕_(L-1) P
-                 if R is important then
-                     push R on Cstack
-                     Locate (prefix(R, L-1), CPL') in PrefDir and insert R in CPL'
-                     Locate (suffix(R, L-1), CPL") in SuffDir and insert R in CPL"
-                     goto new_current_pattern
-                 end-if
-             end-while
-         end-if
-         if support(P) = i and IsMaximal(P) then
-             report P
-         end-if
-     end-while
- end-for
```

The predicate function IsMaximal(P=(P, List$_{S(P)}$)) checks if P is a maximal pattern. It does so by comparing P to all the compound patterns Q=(Q, List$_{S(Q)}$) where Q is an already reported maximal pattern with List$_{S(Q)}$=List$_{S(P)}$=I. All that we need to check is that for no such Q does there exist a number h so that the the patterns P, Q are h-compatible. It is a property of our method that any non-maximal pattern P will be generated after the maximal pattern Q that supersedes it. So, if P is indeed non-maximal, it will be intercepted by the procedure described above and will not be reported.

The pattern discovery method of the present invention can also be used to solve the following problem:

Problem 2: "Given a set S={$s_1, s_2, \ldots, s_m$} of one or more sequences $s_i$ over an alphabet $\Sigma$ of letters, and positive integers L, W and K, find all <L,W> patterns with offset lists of size at least K."

This problem takes into account the case of multiple occurrences of a pattern in one or more of the sequences of the input. Notice that since a pattern P can match a string at more than one offsets, the size of List$_{S(P)}$ cannot be any smaller than the number of sequences matched by P.

The only modification needed so that the pattern discovery method described above be able to handle this problem too, refers to the definition of the notion of "importance". In the context of Problem 2, a pattern (elementary or otherwise) is deemed important if its offset list contains at least K offsets. Other than that, the method applies as already described.

The pattern discovery method of the present invention may be used in a number of applications as set forth below.

Efficient and Accurate Determination of Very Weak Similarities Among Sequences of Events By very weak similarities we mean cases where the patterns that are shared by these sequences contain a lot of "don't care" characters compared to the spatial extent of the patterns.

This is a particularly interesting case. Any method that relies on pair-wise string alignment in order to determine the existence of patterns across two or more sequences is implicitly making the assumption that such an alignment exists. But frequently, a set of sequences may have an intersection but not a substantial alignment. In such cases, alignment-based approaches will fail to identify the weak patterns that are shared among the event sequences. The absence or presence of an alignment is directly related to alignment scores and thresholds. Typically, if the score resulting from an alignment is below a preset threshold the alignment under consideration is discarded. So, although there is no alignment for the current selection of the threshold, there is however an "intersection," i.e. a collection of positions with their respective events that is shared by both strings under examination.

Unlike alignment-based methods, approaches that rely on "enumeration" will find such common patterns but are bound to require a large number of time steps due to the (typically larger) span of the common weak patterns. To appreciate this statement, one can consider the case where two sequences share 4 events that span a window of 100 positions. This means that there is a total of 96 don't care characters. Any algorithm performing blind enumeration of the space would require roughly $(C+1)^{100}$ time-steps before encountering the common pattern; here, C is the cardinality of the alphabet set (=events).

Determination of Patterns Repeating Within One Event Stream

Given a single event stream it is very likely that it contains patterns that occur at least twice. For example, if the event stream represents items purchased during a period of several months by a certain customer of a certain supermarket, then it is possible it contains repeating patterns that correspond to the customer's buying behavior, e.g. he/she purchases only the sale items. Or, the event stream could correspond to medical form claims made to a health insurance carrier by an insured member over a period of several years: if the person has a chronic condition, he/she will have carried out the same tests and received the same prescriptions more than once during the period under consideration. In both cases, direct application of the outlined method would have determined the described behavior.

Automated Determination of Models Describing Sets of Events And Subsequent Class Generation Without loss of generality we assume that the database under consideration comprises a collection S of one or more sequences $s_i$ over an alphabet $\Sigma$. The task is that of determining models for one or more subsets of sequences (=streams) in S.

For example, a group of people are asked to provide answers to a set of questions relating to peoples' preferences: what is your hobby (-ies)? do you like the theater? do you like the movies? what car do you drive? what is your favorite type of music? etc. The answers to these questions generate a fixed length set of events, with each event being the answer to respective question. Each person is then associated with an event stream. Identifying patterns of events shared across subsets of the people polled give rise to models of preference that more or less describe the respective subset, for example, the same hobby, music preference, car driven and magazine subscription could be shared by a group of people who in real life are business and industry professionals. In essence, the respective discovered pattern of events provides a model describing more or less accurately this group of people. And in the general formulation of the problem, each of the discovered patterns would provide a model that accurately describes a subset of sequences contained in S.

Once a model is available for a subset of sequences in S, the model can be treated as a representative of a "class" which contains the sequences described by the model. Clearly, there will be as many classes as there is models. Moreover, some of the classes may have a non-empty intersection and thus share one or more members.

Classification and Very Fast Searches (I.e. Matching) in Databases

Directly related to the automated determination of classes in a database of event streams are the issues of classification and matching. Let us assume that we were given a set S of sequences which were classified as described previously. First, the described method is used to derive the classes in S and the associated models as described above. Then, when given a new sequence $S_{new}$ that is not in S, one can effectively use the derived models to effectively assign the sequence to one of the existing classes (=classification).

But the determination of such a classification also allows to search for the new sequence $s_{new}$ in the database S and report the sequences that match it. Indeed, one need only observe that searches in the database S for member-sequences that match the query (either exactly or approximately) boil down to identifying the appropriate class in the database of whose the query would have been a member had it been present when the classes were initially formed. In principle, there will be fewer classes in S than there is sequences thus providing improvements in the computational burden that such searches impose.

While the invention has been described in connection with specific embodiments, it will be understood that those with skill in the art may develop variations of the disclosed embodiments without departing from the spirit and scope of the following claims.

We claim:

1. A program storage device readable by a machine, tangibly embodying a program of instructions executable by the machine to perform method steps for discovering patterns in at least one sequence of characters, said method steps comprising:

identifying a set of proper templates;

identifying a first set of patterns based on said set of proper templates and said sequence of characters, wherein each pattern within said first set of patterns is contained within said sequence of characters; and combining patterns within said first set of patterns to form a second set of patterns, wherein each pattern within said second set of patterns is contained within said sequence of characters.

2. The program storage device of claim 1, wherein said second set of patterns is non-redundant.

3. The program storage device of claim 1, wherein said second set of patterns comprise a set of all non-redundant patterns contained within said sequence of characters.

4. The program storage device of claim 1, wherein each pattern within said second set of patterns satisfies a predetermined criterion.

5. The program storage device of claim 4, wherein said predetermined criterion comprises one of a minimum number of occurrences and a maximum number of occurrences.

6. The program storage device of claim 4, wherein said predetermined criterion comprises one of a minimum length and a maximum length.

7. The program storage device of claim 1, further comprising the step of reporting a subset of said second set of patterns to a user via an input/output device.

8. The program storage device of claim I, wherein each template within said proper set of proper templates is defined by data representing a sequence of characters over an alphabet $\{0,1\}$.

9. The program storage device of claim 1, wherein each pattern is associated with a first field that identifies characters of said pattern.

10. The program storage device of claim 1, wherein each pattern is associated with a an offset list that comprises a set of offset identifiers each identifying offset of an occurrence of characters of said pattern within said sequence of characters.

11. The program storage device of claim 1, wherein convolvable patterns within said first set of patterns are combined to form said second set of patterns.

12. The program storage device of claim 11, further comprising the step of:

identifying a third set of patterns within said second set of patterns, wherein each pattern within said third set satisfies a predetermined criterion.

13. The program storage device of claim 12, wherein, for each pattern P within said third set of patterns, said predetermined criterion requires that number of occurrences of said pattern P within said sequence of characters is greater than a predetermined minimum number of occurrences.

14. The program storage device of claim 12, wherein, for each pattern P within said third set of patterns, said predetermined criterion requires that number of occurrences of said pattern P within said sequence of characters is less than a predetermined maximum number of occurrences.

15. The program storage device of claim 12, wherein, for each pattern P within said third set of patterns, said predetermined criterion requires that said pattern P has a length greater than a predetermined minimum length.

16. The program storage device of claim 12, wherein, for each pattern P within said third set of patterns, said predetermined criterion requires that said pattern has a length less than a predetermined maximum length.

17. The program storage device of claim 12, further comprising the step of reporting said third set of patterns to a user via an input/output device.

18. The program storage device of claim 12, wherein the combining step combines patterns that are convolvable under the operator $\oplus_R$.

19. The program storage device of claim 12, further comprising the step of identifying a value L, and wherein the combining step combines patterns that are convolvable under the operator $\oplus_{L-1}$.

20. A program storage device readable by a machine, tangibly embodying a program of instructions executable by the machine to perform method steps for discovering patterns in a sequence of characters, said method steps comprising:

identifying a first set of patterns, wherein each pattern within said first set of patterns is contained within said sequence of characters; and combining convolvable patterns within said first set of patterns to form a second set of patterns, wherein each pattern within said second set of patterns is contained within said sequence of characters.

21. The program storage device of claim 20, further comprising the step of:

identifying a third set of patterns within said second set of patterns, wherein each pattern within said third set satisfies a predetermined criterion.

22. The program storage device of claim 21, wherein, for each pattern P within said third set of patterns, said predetermined criterion requires that number of occurrences of said pattern P within said sequence of characters is greater than a predetermined minimum number of occurrences.

23. The program storage device of claim 21, wherein, for each pattern P within said third set of patterns, said predetermined criterion requires that number of occurrences of said pattern P within said sequence of characters is less than a predetermined maximum number of occurrences.

24. The program storage device of claim 21, wherein, for each pattern P within said third set of patterns, said predetermined criterion requires that said pattern P has a length greater than a predetermined minimum length.

25. The program storage device of claim 21, wherein, for each pattern P within said third set of patterns, said predetermined criterion requires that said pattern has a length less than a predetermined maximum length.

26. The program storage device of claim 21, further comprising the step of reporting said third set of patterns to a user via an input/output device.

27. The program storage device of claim 20, wherein the combining step combines patterns that are convolvable under the operator $\oplus_R$.

28. The program storage device of claim 27, further comprising the steps of:

i) storing at least one pattern belonging to said first set of patterns in a stack;

ii) selecting a pattern P stored in a top entry of said stack;

iii) identifying a set Q of patterns, wherein each pattern within said set Q is convolvable with said pattern P under said operator $\oplus_R$;

iv) ordering said set Q of patterns according to a predetermined ordering scheme;

v) traversing through said ordered set of patterns and determining whether a given pattern within said set of ordered patterns satisfies a first predetermined criterion; and vi) if said given pattern satisfies said first predetermined criterion, combining said given pattern with said pattern P to form a combined pattern, storing said combined pattern as a top entry in said stack, and returning to step ii) to process said combined pattern.

29. The program storage device of claim 28, wherein said first predetermined criterion comprises one of a minimum number of occurrences and a maximum number of occurrences.

30. The program storage device of claim 29, wherein each pattern is associated with an offset list that comprises a set of offset identifiers each identifying offset of an occurrence of said characters of said pattern within said sequence of characters; and wherein number of occurrences of a pattern is determined by number of offset identifiers in said offset list associated with said pattern.

31. The program storage device of claim 28, wherein said first predetermined criterion comprises one of a minimum length and a maximum length.

32. The program storage device of claim 31, wherein each pattern is associated with a first field that identifies characters of said pattern;

wherein length of a pattern is determined by calculating number of characters in said first field associated with said pattern.

33. The program storage device of claim 28, wherein each pattern is associated with a first field that identifies characters of said pattern and is associated with an offset list that comprises a set of offset identifiers each identifying offset of an occurrence of said characters of said pattern within said sequence of characters; and wherein, for a combined pattern corresponding to patterns P1 and Q1, said first field identifies characters of said patterns P1 and Q1 that make up said combined pattern, and said offset list comprises a set of offset identifiers each identifying offset of an occurrence of said characters of said combined pattern within said sequence of characters.

34. The program storage device of claim 33, wherein, for each pattern P' within said third set of patterns, said second predetermined criterion requires that said pattern P' is maximal.

35. The program storage device of claim 28, further comprising the steps of:

vi) if the set of ordered patterns is empty or no pattern within the ordered set of patterns satisfies said first predetermined matching criterion, adding pattern P to said third set of patterns if pattern P satisfies a second predetermined criterion, removing the entry corresponding to the pattern P from the stack, and returning to step ii) to process the top entry of the stack until the stack is empty.

36. The program storage device of claim 28, wherein, in step iv), said predetermined ordering scheme orders said set Q of patterns such that maximal patterns are generated before non-maximal patterns.

37. The program storage device of claim 36, wherein said predetermined ordering scheme orders said set Q of patterns according to a prefix relation.

38. The program storage device of claim 37, wherein said prefix relation dictates that any pattern P1 is listed before any other pattern Q1 when $P1 \leq_{pf} Q1$.

39. The program storage device of claim 36, wherein said predetermined ordering scheme orders said set Q of patterns according to a suffix relation.

40. The program storage device of claim 39, wherein said suffix relation dictates that any pattern P1 is listed before any other pattern Q1 when $P1 \leq_{sf} Q1$.

41. The program storage device of claim 20, wherein said first set of patterns are identified by:

identifying a set of templates;

identifying a set of patterns based on said set of templates and said sequence of characters, wherein each pattern within said set of patterns is contained within said sequence of characters.

42. The program storage device of claim 41, wherein each template within said set of templates is a proper template.

* * * * *